(12) United States Patent
Chen et al.

(10) Patent No.: US 9,696,278 B2
(45) Date of Patent: Jul. 4, 2017

(54) PORTABLE RAPID DETECTION DEVICE FOR HEAVY METAL IONS AND METHODS OF USE

(71) Applicant: Nanjing Tech University, Nanjing (CN)

(72) Inventors: Guosong Chen, Nanjing (CN); Ying Hong, Nanjing (CN); Xiaohua Lu, Nanjing (CN); Chang Liu, Nanjing (CN); Xiaoyun He, Nanjing (CN); Dandan Lv, Nanjing (CN); Jikui Wang, Nanjing (CN); Meihua Tang, Nanjing (CN); Zhiyi Zhang, Nanjing (CN); Xiaochen Dong, Nanjing (CN)

(73) Assignee: NANJING TECH UNIVERSITY, Nanjing (CN)

( * ) Notice: Subject to any disclaimer, the term of this patent is extended or adjusted under 35 U.S.C. 154(b) by 31 days.

(21) Appl. No.: 14/994,479

(22) Filed: Jan. 13, 2016

(65) Prior Publication Data

US 2017/0089861 A1    Mar. 30, 2017

(30) Foreign Application Priority Data

Sep. 29, 2015 (CN) .......................... 2015 1 0633166

(51) Int. Cl.
*G01N 27/48* (2006.01)
*G01N 27/42* (2006.01)

(52) U.S. Cl.
CPC ............ *G01N 27/48* (2013.01); *G01N 27/42* (2013.01)

(58) Field of Classification Search
CPC .............................. G01N 27/48; G01N 27/42
See application file for complete search history.

(56) References Cited

U.S. PATENT DOCUMENTS

| 2008/0087544 | A1* | 4/2008 | Zhou ...................... G01N 27/48 204/406 |
| 2010/0072079 | A1* | 3/2010 | Le Ninivin ............ G01N 27/48 205/775 |

\* cited by examiner

*Primary Examiner* — J. Christopher Ball
(74) *Attorney, Agent, or Firm* — CBM Patent Consulting, LLC

(57) ABSTRACT

A portable rapid detection device for heavy metal ions includes a card electrode and a thin-layer flow cell, wherein a three-electrode system of the card electrode is inserted in a micro-channel of the thin-layer flow cell; and heavy metal ions are detected by using an anodic stripping voltammetry (ASV), a solution to be detected flows by the surface of a working electrode in the micro-channel, and heavy metals are enriched and stripped on the surface thereof.

19 Claims, 25 Drawing Sheets

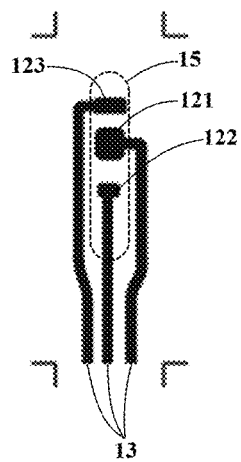
FIG. 31
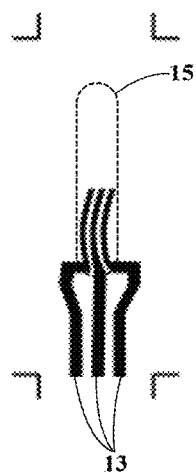 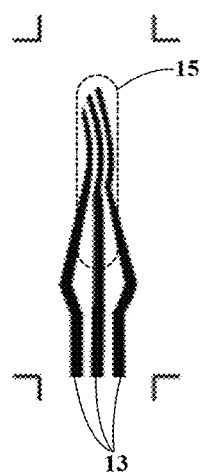 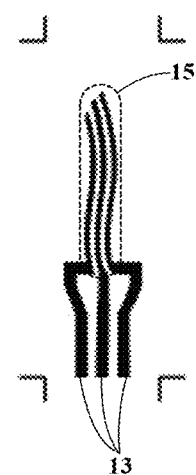
FIG. 32A　　　FIG. 32B　　　FIG. 32C

PORTABLE RAPID DETECTION DEVICE FOR HEAVY METAL IONS AND METHODS OF USE

This application claims priority to Chinese Patent Application Ser. No. 201510633166.1 filed 29 Sep. 2015.

TECHNICAL FIELD

The present invention relates to the technical field of chemical analysis, in particular to a portable detection device capable of rapidly detecting the concentration of trace heavy metal ions in a solution. The present invention further relates to an application method of the device in anodic stripping voltammetric analysis.

BACKGROUND ART

In recent decades, the global electrical and electronics industry brings increasing convenience and benefits to the human society, and also brings mountain-like e-waste and severe environmental pollution to the human society, and this leads to quite severe impact on global ecological environment. The globe has been faced with serious sustainable development issues, countries actively take measures to control the pollution and damage caused by electronic products to the ecological environment, for instance, the European Union has issued the RoHS directive to limit the use of certain hazardous materials in electrical and electronic devices that entering the European market, the limited devices generally include all electrical and electronic devices that may be used in daily life, and the limited hazardous materials include heavy metals, such as lead (Pb), cadmium (Cd) and mercury (Hg). A huge amount of requirements on heavy metal detection are produced under the pressure of environmental protection requirement. At present, the pretreatment technologies of electrical products, such as microwave digestion, are already very mature, are suitable for batch treatment of about 10 to 100 products and are also suitable for field detection owing to low requirements of equipment upon environmental fields, however, digested solutions still need large instruments for analysis, field detection efficiency of heavy metal ions in the solutions is difficult to improve, and how to provide convenient, rapid and low-cost field detection of the heavy metal ions is a technical problem that is faced.

Traditional element test methods include atomic absorption spectrometry and inductively coupled plasma atomic emission spectrometry, while detection instruments of these methods need larger operating space and fit operating environments, have high requirements on power supplies and require matching devices such as ventilating systems and gas cylinders, some instruments further demand circulatory cooling water systems, and in total, the cost is high, detection sample consumption is high, manpower resources are consumed and the instruments are unsuitable for rapid field detection. As an electrochemical analytical method, anodic stripping voltammetry (ASV) has a detection limit up to a ppb-ppt level and fully meets the requirement on sensitivity of heavy metal ion detection, and providing rapid field detection of the heavy metal ions based on the ASV is a technical development direction to be reckoned with.

In traditional ASV detection, a three-electrode system is used to carry out detection in a beaker, three electrodes include an operating electrode (usually a hanging mercury electrode or mercury film electrode), a counter electrode (usually a strip platinum wire electrode), and a reference electrode (usually a rod calomel electrode or silver-silver chloride electrode), and in the beaker, heavy metal ion solution to be detected is contained. During detection, a voltage is applied among the electrodes, and pre-electrolysis is carried out first to allow heavy metal ions in the solution to be reduced to separate out metal which is enriched on the surface of the operating electrode; stripping is performed then to allow heavy metal ions to be detected, which deposit on the surface of the operating electrode, to be oxidized into ions which are stripped, and concentration of the heavy metal ions to be detected may be detected through a current peak value obtained from a stripping voltammetry curve. Although the ASV analytical technique is capable of detecting trace heavy metal ions in a sample solution, a detection process using the traditional methods has the defects that consumption of the sample solution is high, pre-electrolysis time is long and detection results are poor in reproducibility.

In the Development of High-Sensitivity Series Microchannel Thin-Layer Flow Cell and Application Thereof in Urine Lead Determination written by Tan Xuefei, Zhang Rong, et al. and published on the second issue of Chemical Reagents in 2012, heavy metal ion detection in a stripping voltammetry method through cooperation of a micro-channel thin-layer flow cell and a three-electrode system is disclosed. Due to the application of the micro-channel thin-layer flow cell, the enrichment efficiency is improved. However, among the used three electrodes, the working electrode adopts the glassy carbon mercury membrane electrode. Apart from serious toxic effects of mercury contained in the electrode, the glassy carbon mercury membrane electrode needs to be demounted for glassy carbon polishing and other pretreatment work which is complex and makes continuous work difficult to realize; the reference electrode adopts the traditional rod-like saturated calomel electrode which contains potassium chloride solutions and crystals thereof, is complex in structure and also contains hazardous substances of mercury and calomel. The above defects limit application of the technology in field rapid detection. In particular, mercury in the electrodes has severe toxicity which heavily pollutes the natural environment.

In two reference documents "Environmentally friendly disposable sensors with microfabricated on-chip planar bismuth electrode for in situ heavy metal ions measurement" (<Sensors and Actuators B>134 (2008)) and "Potentiometric and voltammetric polymer lab chip sensors for determination of nitrate, pH and Cd (II) in water" (<Talanta>83 (2010)) written by Zhiwei Zou, Am Jang et al., a laboratory sensor chip for in situ detection of heavy metal ions is disclosed. According to the laboratory sensor chip, two groups of small-sized sensor electrodes are connected in a micro-channel in series; the micro-channel is a saddle-shaped thin layer cavity; a direct-through to-be-detected solution inlet and a direct-through to-be-detected solution outlet are arranged at two ends of the micro-channel respectively; each group of electrodes adopts a three-electrode system, wherein the working electrode is a bismuth electrode, the counter electrode is a gold electrode, the reference electrode is a silver-silver chloride electrode, and leads for connecting all the electrodes are arrayed to form a contact zone. The in situ heavy metal ion detection method based on the lab-on-a-chip idea realizes miniaturization of ASV detection instruments by using the micro electro mechanical system technology, and avoids environment pollution caused by application of mercury electrodes. However, since the whole testing process is started instantly after the thin-layer micro cell is filled with solutions, the solutions keep static in the whole testing process and the enrichment efficiency is not high; besides, since the laboratory sensor chip works in a way that two groups of electrodes are connected in series, and flow field distribution and the relation between flow field distribution and effective working surfaces of the electrodes are not considered at all, the enrichment operation time is prolonged and error generating links are increased.

In view of the status of the prior art described above, to meet field rapid detection requirements of large batches of heavy metal ion samples, it is urgent to develop a simple, portable, efficient, environment-friendly and inexpensive heavy metal ion rapid detection technology based on the ASV.

SUMMARY OF THE INVENTION

The objective of the present invention is to overcome the defects of the prior art, combine card electrodes with a thin-layer micro-cell flow technology, associate the shape of the electrodes with the shape of a flow field to improve the analysis property, and provide a portable rapid detection device for heavy metal ions and a use method thereof, wherein the portable rapid detection device for heavy metal ions and the use method thereof can conveniently and effectively achieve high-sensitivity field detection for the heavy metal ions.

In order to solve the above problems, the technical solution of the rapid detection device for the heavy metal ions is that:

a portable rapid detection device for the heavy metal ions comprises a card electrode and a thin-layer flow cell, wherein the card electrode comprises a substrate and a three-electrode system; the three-electrode system comprises a working electrode, a counter electrode and a reference electrode which are planar all-solid-state electrodes distributed on the substrate; one end of the substrate is an interface end, contact pins are distributed on the interface end, and the three contact pins are respectively connected with the three electrodes of the three-electrode system; the thin-layer flow cell is of an integrally formed structure and comprises a cell wall, a micro-channel and an electrode socket; the micro-channel is a thin-layer-shaped cavity enclosed by the cell wall, and the micro-channel is connected with a liquid inlet pipeline and a liquid outlet pipeline which lead outwards; the electrode socket is an opening of the micro-channel on the cell wall, and the card electrode can be inserted in and pulled out of the electrode socket; the card electrode is inserted in the thin-layer flow cell from the electrode socket, the three-electrode system stretches into the micro-channel, and the interface end extends out of the cell wall. During detection, the card electrode voltage is applied to the card electrode via the interface end, and the electric current is detected via the interface end.

Preferably, the card electrode is printed by using a silk-screen printing method.

Preferably, the contact pins are arranged at the interface end in parallel, and the sizes of the contact pins are consistent with that of a standard USB interface. Due to the fact that the interface end is used for connecting a power supply, and the USB interface is the most commonly used power supply interface, the contact pin, together with USB, is designed to be of the same size for convenience of detection.

Preferably, the working electrode is a silver-carbon electrode, the counter electrode is a silver electrode, and the reference electrode is a silver-silver chloride electrode.

Preferably, the planar shape of the micro-channel can be chosen in a variety of ways as desired, such as a rectangular shape, a saddle shape, an oval shape or a circular shape.

More preferably, a cavity of the micro-channel is saddle-shaped, and the liquid inlet pipeline and the liquid outlet pipeline are respectively connected with the micro-channel at two top ends of the saddle-shaped cavity along the tangential direction. It can also be chosen in a direction where a communication position formed other angles with an edge of the micro-channel.

Preferably, the liquid inlet pipeline and the liquid outlet pipeline respectively have a pipeline orifice protruding out of the outer wall of the cell wall, and the protruded pipeline orifices are convenient for connecting a hose during detection.

Preferably, the thickness of the micro-channel is 0.8 mm to 1.2 mm, and the inside diameters of the liquid inlet pipeline and the liquid outlet pipeline are less than or equal to the thickness of the micro-channel.

More preferably, the thickness of the micro-channel is 0.9 mm, and the inside diameters of the liquid inlet pipeline and the liquid outlet pipeline are 0.83 mm.

Preferably, the thin-layer flow cell is made of photosensitive resin, which is prepared with a stereo lithography in a 3D printing technology.

Preferably, three electrodes of the three-electrode system are distributed on the substrate along the solution to be detected in the micro-channel. When the micro-channel cavity is saddle-shaped, and the liquid inlet pipeline and the liquid outlet pipeline are respectively connected with the micro-channel at the top of either end of the saddle-shaped cavity along the tangent line direction, the flow field in the micro-channel is S-shaped, the three electrodes are distributed along the S shape, the electrodes can only be distributed in the lower half part of the S shape or the upper half part of the S shape, and most preferably is distributed across the S-shaped region.

More preferably, in the three electrodes distributed along the shape of the flow field, widths of the working electrode and the reference electrode are greater than that of the counter-electrode.

The technical solution of the application method of the detection device of the present invention is:

The application method of the afore-mentioned detection device comprises the following steps:

(1) assembly of the detection system: connecting the liquid inlet pipeline and the liquid outlet pipeline of the thin-layer flow cell to the liquid inlet hose and the liquid outlet hose, respectively, wherein the liquid inlet hose extends into the solution to be detected and is provided with a peristaltic pump, and connecting the interface end of the card electrode with the corresponding interface of the electrochemical analysis workstation;

(2) an enrichment process: adjusting the electrochemical analysis workstation, and applying an enrichment voltage between the working electrode and the reference voltage; starting the peristaltic pump, driving the solution to be detected to flow into the thin-layer flow cell from the liquid inlet pipeline for pre-electrolysis, and discharging waste liquid from the liquid outlet pipeline; after the pre-electrolysis, shutting down the peristaltic pump, and standing the solution to be detected;

(3) a stripping process: adjusting the electrochemical analysis workstation to positively scan the voltage between the working electrode and the reference electrode from a negative direction, so that heavy metals to be detected and enriched on the working electrode are stripped again; and (4) detection data collection: recording the current in the working electrode and an auxiliary electrode circuit and the potential of the working electrode in the stripping process to obtain a stripping voltammetry curve.

Preferably, a $Bi^{3+}$ solution and an acid base solution are added in the solution to be detected and containing heavy metal ions before detection.

More preferably, the concentration of $Bi^{3+}$ in the solution to be detected is 500 μg/L.

More preferably again, the acid base solution is a 0.1 mol/L NaAc—HAc solution, and the pH of the solution to be detected is adjusted to be 4.6.

Preferably, in the enrichment process, the flow rate of the solution to be detected in the liquid inlet pipeline is set as 0.02 m/s to 0.05 m/s.

Preferably, in the enrichment process, the enrichment voltage is −1.2V, the enrichment time for finishing the enrichment process is 180 s, and the enrichment time contains a standing time of 60 s.

Preferably, in the stripping process, the voltage is scanned by square waves, and the potential increment is 0.005V.

The portable rapid detection device for heavy metal ions provided by the technical solution of the present invention combines the thin-layer micro-area flow technology with the ASV, uses the planar all-solid-state card electrode and adopts the 3D printing technology to manufacture device assemblies, in order to perfect the detection method for heavy metal ions, and the portable rapid detection device for heavy metal ions has the following advantages:

1. the portable rapid detection device for heavy metal ions provided by the present invention drives the solution to be detected to enrich in a flow state and strip in a stationary state, which guarantees a fresh and high-concentration raw solution to continuously flow by the surface of the electrode in the enrichment process to improve the enrichment efficiency;

2. the present invention provides a lead ion and cadmium ion selective sensor with high performance and low cost, the three electrodes are purely planar all-solid-state electrodes, contain no harmful substances and have stable structures, the card electrode can be inserted, pulled out and replaced at any time, no cross contamination between samples is generated, and continuous work is suitable;

3. according to the portable rapid detection device for heavy metal ions provided by the present invention, a planar electrode system following flow field distribution in shape is designed and made, thereby further shortening the enrichment operation time and improving the measurement sensitivity and the working efficiency;

4. the thin-layer flow cell of the portable rapid detection device for heavy metal ions provided by the present invention is formed at one time by 3D printing without needing a jointing component or a pipeline joint of the cell wall; based on the flexibility of the 3D printing technology, a variety of detection channels with micro-sizes and complicated shapes can be conveniently made when the cell wall is printed; and 5. the detection device provided by the present invention is high in integration degree, small in overall size and convenient to carry, and can achieve on-site rapid in-situ detection.

6. in a detection process of the portable rapid detection device for heavy metal ions provided by the present invention, a bismuth film is plated on the same position on the working electrode to ensure a better enrichment effect;

7. When the detection device provided by the present invention is at work, the solution dosage of the microchannel is small, and the necessary solution is generally less than 3 mL, which is much smaller than the solution dosage of 10-100 mL when detecting is performed in a beaker;

8. the portable rapid detection device for heavy metal ions provided by the present invention has good reproducibility, the solution continuously and stably flows in the microchannel to carry out ASV detection, stirring is not needed in the entire process, and completely mechanical repeat can be achieved, so that the reproducibility and the accuracy of concentration detection are guaranteed; and in a traditional three-electrode system, a curve has a large amount of irregular burs, while the enrichment curve obtained by the thin layer micro-area flow technology provided by the present invention is very smooth.

BRIEF DESCRIPTION OF THE DRAWINGS

FIG. 31 is a design diagram of a conventional tri-electrode of the card electrode in the present invention;

FIG. 32A is a design diagram of an S-shaped tri-electrode improved by the present invention, wherein the electrode is the lower part of an S shape;

FIG. 32B is a design diagram of an S-shaped tri-electrode improved by the present invention, wherein the electrode is the upper part of the S shape;

FIG. 32C is a design diagram of an S-shaped tri-electrode improved by the present invention, wherein the electrode is the entire S shape;

Figure 1:
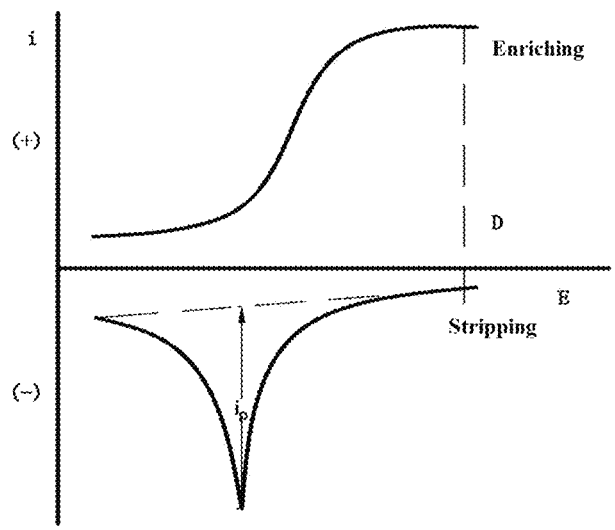
FIG. 1 is a stripping voltammetry curve detected by ASV.

In the drawings above:
1: Card electrode; 11: Substrate; 121: Working electrode; 122: Counter electrode; 123: Reference electrode; 13: Contact pin; 14: Interface end; 15: Micro-channel region; 2: Thin-Layer flow cell; 21: Cell wall; 22: Micro-channel; 221: Liquid inlet pipeline; 222: Liquid outlet pipeline; 23: Electrode socket; Z1, Z2: Ideal working zone.

DETAILED DESCRIPTION OF THE INVENTION

The present invention will be further described through embodiments in conjunction with the accompanying drawings for a better understanding of the present invention.

The present invention uses ASV to detect the concentration of heavy metal ions in a solution, and the detection method is a kind of voltammetry in electrochemical analysis. Voltammetry is a sort of method which is developed on the basis of classical polarography based on electrolysis and is characterized by measuring a voltammetry curve in an electrolysis process. A new-type stripping voltammetry analysis technique is formed in conjunction with controlling potential and electrolysis to enrich on the basis of the voltammetry, has a detection limit which can reach a ppb-ppt level, and can be applicable to the analysis and detection of over 30 elements. An analysis process of stripping voltammetry is divided into two parts of enrichment (pre-electrolysis) and stripping, and is divided into ASV and cathodic stripping voltammetry (CSV) according to stripping reactions happening on different electrodes, wherein, the ASV is applicable to measuring metal ions, and is a common method of heavy metal detection because of its extremely low cost and high sensitivity.

An general ASV detection voltammetry curve is shown in FIG. 1, and the basic principle of which is:

carrying out pre-electrolysis with the working electrode serving as a cathode, controlling the potential of the cathode to be in the potential range of limiting diffusion currents of the detected heavy metal ion $M^{n+}$ to be detected (generally 0.2V to 0.3V negative to the half-wave potential $E_{1/2}$, corresponding to the D position in FIG. 1), and reducing $M^{n+}$ into metal which is enriched on the working electrode, wherein an example is that when the working electrode adopts a traditional hanging mercury electrode, $M^{n+}$ is reduced into metal M which enters the hanging mercury electrode to generate amalgam, and the reaction on the hanging mercury electrode is:

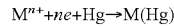
$M^{n+}+ne+Hg \rightarrow M(Hg)$ since the pre-electrolysis process is carried out during stirring, stopping stirring on the condition of continuously applying voltage onto the electrodes after pre-electrolysis so that the substance to be detected M enriched on the surface of the hanging mercury electrode can be uniformly distributed in mercury quickly; stripping the M after standing for 0.5 min to 1 min, scanning the potential of the hanging mercury electrode from the negative direction to the positive direction at constant speed so as to re-oxidize, by an anode, M(Hg) sedimented on the hanging mercury electrode into ion $M^{n+}$ which enters the solution; recording stripping currents in the stripping process and making a potential diagram which enables determination of concentration of the metal substance to be detected according to the peak height of the voltammetry curve at the time of stripping.

Figure 2:
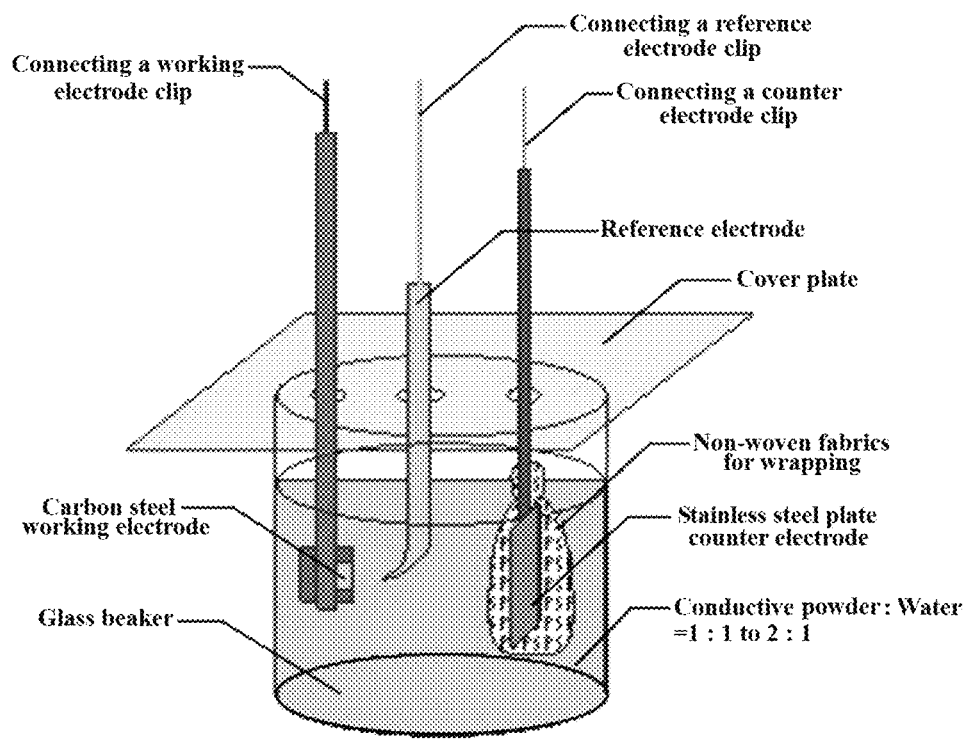
FIG. 2 is a schematic diagram of an ASV detection device of a traditional three-electrode system.

The traditional ASV device is shown in FIG. 2, wherein a three-electrode system composed of a working electrode, a reference electrode and a counter electrode is inserted into a beaker containing a solution with trace heavy metal ions for detection. During detection, a voltage is applied between the working electrode and the reference electrode at first, when the potential of the working electrode is higher than the separation potential of the heavy metal ions to be detected, the heavy metal ions in the solution are reduced and separated out on the surface of the working electrode (similar to an electrolysis or electroplating process), and the longer the potential applying time on the working electrode is, the more the reduced metal deposited on the surface of the working electrode are, the process is called the pre-electrolysis process of enriched heavy metal to be detected, as shown in an enrichment voltammetry curve for a current negative area in FIG. 1. When sufficient metal is enriched, the stripping process is carried out after the solution keeps standing for a certain time. When forward voltage is added on the working electrode, the metal deposited on the surface of the working electrode is oxidated and stripped. Currents in a loop formed by the working electrode and the counter electrode in the process of adding forward voltage on the working electrode are detected continuously, and corresponding potentials of the working electrode are recorded, as shown by the stripping voltammetry curve of the current forward area in FIG. 1, and a µA-level or smaller peak current $i_p$ can be detected. If the heights of all operation conditions are identical, the peak current $i_p$ and the concentration of metal ions to be detected in the solution are only in linear positive correlation, and the concentration to be detected can be acquired by comparing with a standard solution having the same condition as the solution containing the metal ions.

The traditional ASV detection device described above can be used to detect trace heavy metal ions in a sample solution, and has relatively high sensitivity. However, the detection process that is generally conducted in a beaker has many defects: 1. The dosage of the sample solution is large. Generally, at least 10 mL to 100 mL of solution is required for the detection that is conducted in the beaker, moreover, the three electrodes of the three-electrode system need to be fully submerged in the solution, which brings great inconvenience to a precious sample or a sample for which the mass collection is not suitable. 2. The time for pre-electrolysis is long. Generally, the time required for pre-electrolysis ranges from several minutes to half an hour. This is because once the electrolysis process is begun, the heavy metal ions in the solution which contacts with an electrode surface will be rapidly exhausted, and the electrolysis process will be stopped before the heavy metal ions in the solution spread from the bulk of the solution to the electrode surface to serve as supplements. It is worth noting that the spreading process is slow. Therefore, a relatively long time for pre-electrolysis is required so that a large quantity of heavy metals to be detected which are enough for detection can be enriched on the electrode surface. 3. The reproducibility is poor. To solve the problem that the time for pre-electrolysis is overlong, the stirring way is generally adopted to help heavy metal ions spread from the bulk of the solution to the electrode surface. During multiple operations, the positions of electrodes, the states of stirrers and the forms of eddies are hardly completely identical, and both the enrichment amount of the heavy metal ion on the electrode surface and the reproducibility of deposition form are poor. Consequently, the peak value reproducibility of the stripping current is poor, and the linear relationship with concentrations is also poorer.

Figure 3:
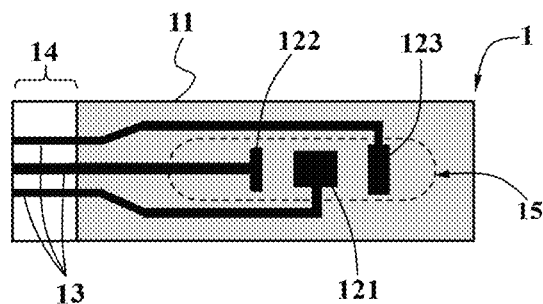
FIG. 3 is a schematic diagram of a structure of a card electrode in a detection device.
Figure 4:
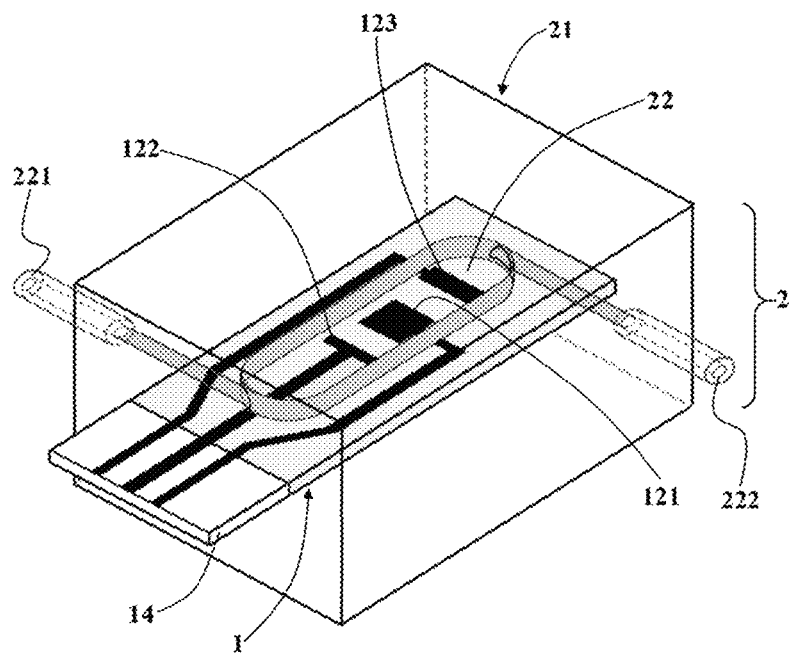
FIG. 4 is a three-dimensional schematic diagram of an overall structure of the detection device.
Figure 5:
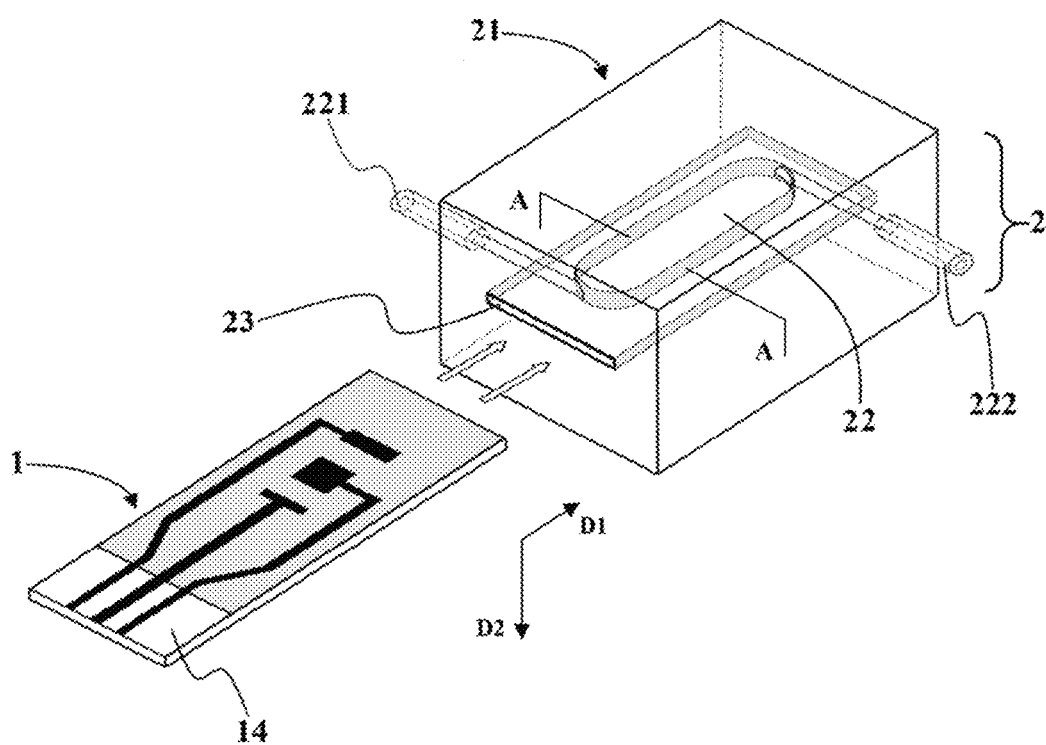
FIG. 5 is a decomposed schematic diagram of a structure of the detection device in FIG. 4.
Figure 6:
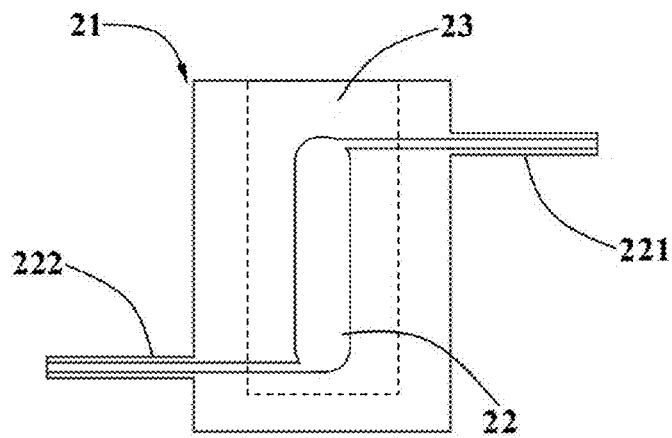
FIG. 6 is an A-A sectional view of a transparent material thin-layer flow cell in FIG. 5.

The present invention provides a portable rapid detection device for heavy metal ions for overcoming the defects existing in the traditional ASV detection device. The basic technical solutions of the detection device of the present invention are shown in FIGS. 3 to 6. The device of the present invention is composed of a card electrode 1 and a thin-layer flow cell 2, wherein:

the card electrode 1 is an all-solid-state three-electrode system which is purely planar, the basic structure of which is shown in FIG. 3, comprising a substrate 11, a working electrode 121, a counter electrode 122, a reference electrode 123 and contact pins 13; one end of the substrate 11 is an interface end 14; the three electrodes and the contact pins 13 are distributed on the substrate 11. Each electrode is connected with one contact pin 13, respectively. The contact pins 13 are arranged in the interface end 14; a working zone of the three electrodes shown in FIG. 3 is in the shape of a square, and leads between the electrodes and contact pins are designed to be commonly used bend lines The card electrode 1 and the thin-layer flow cell 2 constitute the entire detection device whose structural representation is shown in FIGS. 4 and 5, wherein: the thin-layer flow cell 2 comprises a cell wall 21, a micro-channel 22 and an electrode socket 23; the cell wall 21 forms an outer frame of the thin-layer flow cell 2. In this embodiment, the cell wall 21 is made of transparent materials, the overall shape of which is of a transparent rectangular body, and while in other embodiments, non-transparent materials can be selected based on actual needs or other shapes can be designed; the micro-channel 22 is a thin-layer-shaped cavity enclosed by the cell wall 21, and two ends of the cavity are connected with a liquid inlet pipeline 221 and a liquid outlet pipeline 222 that lead outwards, respectively; the electrode socket 23 is an opening of the micro-channel 22 on the cell wall 21. The shape and size of the opening match with the card electrode 1 which can be closely inserted into the electrode socket 23. The inserted card electrode 1 can be pull out and changed; when the card electrode 1 is inserted into the electrode socket 23, a micro-channel area 15 stretches into the micro-channel 22. There are three electrodes in the micro-channel area 15, and the micro-channel 22 and the three electrodes constitute the detection area of heavy metal ions; the card electrode 1 is longer than the electrode socket 23. After the card electrode 1 is inserted, the interface end 14 of the card electrode 1 stretches out of the cell wall 21 to serve as the interface which is electrically connected with the electrochemical work station during detection. As can be seen more clearly from the sectional view of FIG. 6, in this embodiment, the micro-channel 22 is a saddle-shaped cavity, the liquid inlet pipeline 221 and the liquid outlet pipeline 222 are connected respectively to the two top ends of the saddle-shaped cavity of the micro-channel 22, and the pipeline orifice direction of each connection point is tangent to the edge of the cavity at the point; the two pipelines lead outwards through the micro-channel 22, the outer wall of the thin-layer flow cell 2 has projecting pipeline orifices, and the inner diameter of the pipelines is less than or equal to the thickness of the micro-channel 22;

The micro-channel of the detection device of the present invention is not limited to the saddle shape shown in FIGS. 4-6. Based on a thin-layer hollow-cavity structure, the micro-channel also can be designed in various shapes such as a rectangular shape, a circular shape and an oval shape, in which the rectangular shape and the saddle shape are most commonly used. Meanwhile, the connection positions between the liquid inlet pipeline and the micro-channel and between the liquid outlet pipeline and the micro-channel as well as a pipeline orifice direction also have multiple choices. Generally, the liquid inlet pipeline and the liquid outlet pipeline are respectively connected to two opposite ends of the cavity of the micro-channel so as to facilitate the solution to smoothly flow through the entire micro-channel; the pipe orifice direction is generally designed to be a normal direction or a tangent direction of a cavity edge at a connection point, and other directions also can be selected as the pipe orifice direction according to the actual requirement.

The design of the detection device of the present invention employs a micro-fluidic technology, which can effectively overcome defects, existing in detection, of the traditional ASV device. The concept of the micro-fluidic technology is to integrate a traditional classical analysis method and a detection unit into one device, such that each step (such as extraction, separation, purification, etc.) of the analysis detection is enriched into one chip sensor to be completed according to the process. The ultimate goal of the micro-fluidic technology is to establish a lab-on-a-chip based on a micro-fluidic chip and integrating each operation step of the chemical analysis. A micro-fluidic device generally employs the micro-channel to be cooperated with the chip sensor, and fluid in the micro-channel is driven by means of an electric way, a pressure way or a gravity way. The small scale of the micro-channel not only miniaturizes the overall size of an analysis device, but also brings about many micrometer and nanometer effects. Therefore, compared with a traditional analysis system, the analysis performance of the analysis device is remarkably improved; along with the size reduction of the micro-channel, the thermal conductivity and the heat transfer rate of the micro-channel are significantly enhanced, so that fast analysis, separation or other more complicated operation of a sample can be implemented; the size reduction of the micro-channel also can result in less consumption of manufacturing materials, so that the cost of the chip sensor after the mass production is controllably reduced, which facilitates the commercialization of the chip; moreover, the size reduction of the micro-channel leads to less consumption of samples and reagents when the micro-fluidic device is in analysis detection, thus creating a condition for acquiring extremely large unit information quantity by means of parallel analysis. In the detection device of the present invention, the card electrode 1 and the thin-layer flow cell 2 constitute a complete micro-fluidic system. The card electrode 1 is a chip sensor, and the thin-layer flow cell 2 internally includes a micro-channel 22 which is used cooperatively with the card electrode 1.

The traditional ion selective electrode is subjected to the limitation on the aspect of the application range, of which the key lies in a liquid-state internally-filled reference electrolyte. The disadvantages of the ion selective electrode such as inconvenience in carrying, incapability of inversion and intolerance to high temperature and high pressure can be solved by employing an all-solid-state electrode; the card electrode of the detection device is the all-solid-state electrode using the three-electrode system. Three electrodes are a working electrode, a reference electrode and a counter electrode. The three-electrode system has advantages of short enrichment time, high voltage scanning speed, automatic compensation to iR drop, less interference from foreign ions and the like.

A basic structure and material of the three-electrode system of the detection device of the present invention are shown as follows:

The working electrode has low required resistance and large specific surface area, and forms of the working electrode mainly include a mercury electrode and a solid electrode. A traditional working electrode is generally the mercury electrode, mainly including a hanging mercury electrode and a mercury film electrode; the mercury electrode has a high overpotential for hydrogen and a wide range of potential use; as mercury is capable of generating 'amalgam' together with many metals, stripping potential of the metals is decreased and an analytical range is enlarged; however, the mercury is of great toxicity, may cause great pollution to the natural environment, does not meet the requirement on environment protection and has been replaced with solid electrodes step by step. The solid electrode mainly includes a noble metal electrode and a carbon electrode and is still available for use at positive potential, while the mercury electrode may dissolve at positive potential; the carbon electrode has small background current and low price, thus various solid electrodes of carbon material are present. The working electrode 121 in the card electrode 1 of the present invention is a silver-carbon electrode having bottom silver and surface layer carbon.

The counter electrode functions with the working electrode to form a loop allowing passage of current; since the counter electrode is unable to affect responses on the working electrode and has low required resistance and stable surface property, the counter electrode is generally made from stable materials, such as platinum and gold. The counter electrode 122 in the device of the present invention is a silver electrode, and a silver surface layer of a contact pin of the counter electrode is covered with carbon. Resistance of this electrode is determined mainly by bottom layer silver, the resistance of the silver is less than that of gold, a portion having the surface layer covered with the carbon has more stable chemical properties than the gold, and overall cost is lower than that of the gold electrode.

The reference electrode has high required resistance and stable potential, and common reference electrodes include a calomel electrode and a silver-silver chloride electrode. To avoid environmental pollution caused by the use of mercury, the reference electrode 123 in the device of the present invention is made of a purely solid-state silver-silver chloride electrode; an electrode structure is divided into an exposed area and an insulating layer covered area; a bottom layer of the exposed area is of silver, and a surface layer of the exposed area is of silver-silver chloride; a bottom layer of the covered area is of silver while a surface layer of the covered area is of carbon, the silver of the bottom layer of the covered area is not in direct contact with the silver-silver chloride of the exposed area while the carbon of the surface layer of the covered area is in direct contact with the silver-silver chloride, and by changing a distance between the silver of the bottom layer and the silver-silver chloride, the resistance of the reference electrode can be adjusted and controlled to obtain more stable operating potential.

Figure 7:
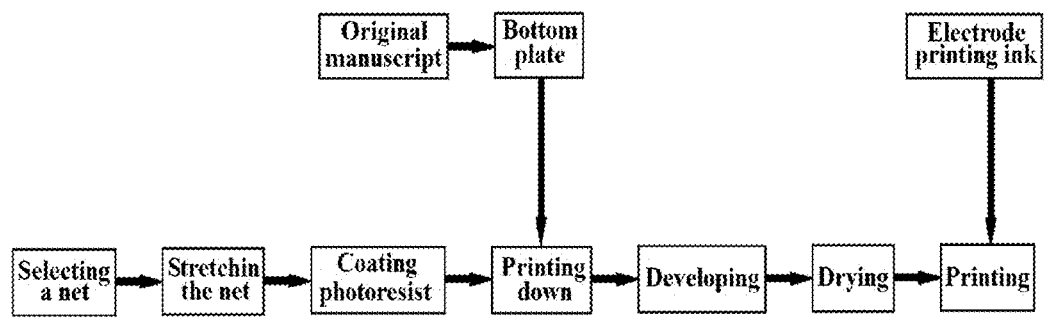
FIG. 7 is a schematic flowchart of a silk-screen printing process of a photosensitive plate making method.

As a technical scheme in the embodiment of the present invention, the card electrode is made by a silk-screen printing technology. The silk-screen printing technology is a main method to produce a disposable electrochemical sensor electrode at present. According to the basic principle of silk-screen printing, meshes of an image portion of a printing plate enable ink to be printed to a substrate by through printing; meshes of the rest of the printing plate are plugged and avoid passing of the ink, and blank is left on the substrate. A key link in the silk-screen printing technology is the producing of the printing plate, manual hollowing-out for plate making is generally used in traditional plate making methods, and a photochemical plate making method (photosensitive plate making method) is generally used in modern practice. In the photochemical plate making method, a silk screen is used as a support and is tensioned on a screen frame, the silk screen is then coated with photoresist to form a photosensitive film, a positive bottom plate is closely attached to the photosensitive film, exposing and developing are carried out, meshes of an image portion, which requires ink penetration, of the printing plate are not closed, and the ink penetrates the meshes during printing to form a pattern on the substrate. The silk-screen printing technology is generally as shown in FIG. 7. Two main classes of ink, silver ink and carbon ink, are used mainly as the ink to print electrodes, and the silver ink is used to print basic rails for manufacturing the electrodes in order to improve the conductivity; the carbon ink is spread on a silver rail in order to prevent contacting between silver and a solution.

A screen printing forme is used as a mold for carrying out silk-screen printing; the size and shape of the to-be-manufactured sensor electrodes can be changed; and the miniaturization and integration of the sensor electrodes are easily realized. Three card electrodes using a silk-screen printing technology can be all conveniently printed on the same plane chip to manufacture a purely planar all-solid-state electrode used in the testing device of the present invention.

The thin-layer flow cell in the testing device of the present invention is manufactured in an integral molding manner; as shown in FIGS. 4 and 5, all structural components of the thin-layer flow cell 2 are the micro-channel 22, the liquid inlet pipeline 221, the liquid outlet pipeline 222 and the electrode socket 23 which are all in integral molding with the cell wall 21, wherein the micro-channel 22 and the electrode socket 23 are formed by the cavity reserved in the cell wall 21 and an opening connected with the cavity, and the liquid inlet pipeline 221 and the liquid outlet pipeline 222 are formed by combining tubular cavities reserved in the cell wall 21 and pipeline orifices projecting at the outer side of the cell wall 21. Joining parts and pipeline joints are omitted among the components, any assembling process is not needed, and the structure is relatively smooth and steady.

As a technical solution of the invention, the 3D printing technology is used for manufacturing the thin-layer flow cell in an integral molding manner According to difference of materials used for printing and manners of generating slice layers, multiple methods are provided for realizing 3D printing, and main technologies comprise fusion deposition molding (FDM) of extrusion molding; direct metal laser sintering (DMLS), electron beam melting (EBM), selective laser sintering (SLS) and the like of granular material molding; stereo lithography appearance (SLA) and digital light processing (DLP) of photopolymerization molding; and laminated board manufacturing (LOM) of laminated molding. Multiple 3D printing technologies are developed and advocated by different companies, and the main differences of the multiple 3D printing technologies lie in printing speeds, cost, selectable materials, color capability and the like.

As a technical solution of the invention, photosensitive resin is used as a 3D printing material and is printed to form the thin-layer flow cell by using a three-dimensional SLA technology, and a PolyJet printing system of the Object company is used for carrying out SLA printing. The PolyJet system is a nozzle printer technology and realizes spraying of photosensitive polymer materials by using a 16-30 micrometer ultra-thin layer at present, and the photosensitive polymer materials are built into a tray layer upon layer until part manufacturing is completed. When each layer of photosensitive polymer is sprayed, the photosensitive polymer is cured by adopting ultraviolet light; and an printed object is a complete solidified model with no need for post curing. Two different types of photosensitive resin materials are used in a molding process of printed workpieces, wherein one type of photosensitive resin material is used for generating a real model; and the other type of photosensitive resin material is a colloid-like resin material for supporting, and the supporting material is precisely added to desired positions such as hanging structures, grooves, complex details and thin walls of a complex molding structure model through process control. When the whole printing molding process is completed, the supporting materials can be easily removed only by using a water gun or by directly putting the supporting materials in a water soluble box, while molding workpieces with neat and smooth surfaces are left in the end. Sample pieces generated by the PolyJet system are delicate in details, smooth in surfaces and very high in accuracy, and the resolution of the sample pieces is better than that of workpieces obtained by using the SLA. The PolyJet system can realize colorful and multi-material printing, can also perform digital material printing, and the post processing of printing is simple and convenient. In addition, the PolyJet technology is the technology capable of printing the workpieces with the highest transparency in the 3D printing at present. The thin-layer flow cell with the relatively good transparency can be manufactured by using the PolyJet technology in the device of the present invention and facilitates observation of reaction conditions of the surface of the electrode in a detection process to realize effective control.

An Eden260vs type 3D printing device in the PolyJet printing system is used for manufacturing a thin-layer flow cell of the present invention, wherein the size of the printing device is 870 mm×735 mm×1200 mm, the maximum molding size is 260 mm×260 mm×200 mm, the printing thickness can be selected from 0.016 mm/0.028 mm/0.030 mm, eight printing heads are respectively M×4 and S×4, the printing precision is 0.1 mm (varying with modeling parameters, a geometrical shape and a placement direction of a model), the surface roughness is 16, processing software is Object Studio, a file format is STL, and multiple molding materials are selectable. VeroClear is used as the molding material for manufacturing the transparent thin-layer flow cell; and a water soluble box supporting scavenging system is used for removing the supporting material.

A basic technical solution of using the detection device of the present invention for detecting heavy metal ions in a solution comprises the following steps:

1. preparation of the solution to be detected: adding a bismuth ion ($Bi^{3+}$) solution and an acid base solution in the solution to be detected and containing the heavy metal ions;

2. assembly of a detection system: connecting the liquid inlet pipeline and the liquid outlet pipeline of the thin-layer flow cell to the liquid inlet hose and the liquid outlet hose, respectively, wherein the liquid inlet hose extends into the solution to be detected and is provided with a peristaltic pump, and connecting the interface end of the card electrode with the corresponding interface of an electrochemical analysis workstation;

3. an enrichment process: adjusting the electrochemical analysis workstation, and applying the negative voltage between the working electrode and the reference voltage; starting the peristaltic pump to drive the solution to be detected to flow into the thin-layer flow cell from the liquid inlet pipeline for pre-electrolysis, and discharging the waste liquid from the liquid outlet pipeline; after completion of pre-electrolysis, shutting down the peristaltic pump, and standing the solution to be detected;

4. a stripping process: adjusting the electrochemical analysis workstation to scan the voltage between the working electrode and the reference electrode from negative to positive, so that heavy metals to be detected and enriched on the working electrode are stripped again; and 5. detection data acquisition: recording the current in the working electrode and an auxiliary electrode circuit and the potential of the working electrode in the stripping process to obtain a stripping voltammetry curve.

The peak current $i_p$ of the solution to be detected is obtained by the stripping voltammetry curve, and the $i_p$ and a peak current value obtained by detecting a standard sample with known concentration under the same conditions are subjected to comparative calculation to obtain the concentration of the solution to be detected.

The operation and relevant parameters affecting detection effects in the above-mentioned steps are respectively detected and analyzed, and the implementation modes of the method are optimized.

According to the above-mentioned basic technical solution, the $Bi^{3+}$ solution is added in the solution to be detected to serve as electrolyte for pre-electrolysis, $Bi^{3+}$ is reduced into metal bismuth (Bi) on the working electrode in a later enrichment process of trace heavy metals determined by ASV, the metal bismuth is combined with the reduced heavy metals to be detected to form a bismuth alloy membrane similar to amalgam, and the bismuth alloy membrane is adsorbed on the surface of the working electrode, thereby forming a peak current in the stripping process. The effect of the bismuth membrane in the ASV detection is similar to that of a mercury membrane in a conventional mercury membrane electrode, and the pollution of high toxicity of mercury to environments can be avoided by replacing the mercury membrane with the bismuth membrane. Two main methods for forming the bismuth membrane are generally provided:

1. A bismuth membrane preplating method: firstly the working electrode is put in a bismuth-containing solution, and the bismuth membrane is preplated under the condition of constant potential. As $Bi^{3+}$ is easily hydrolyzed under the conditions of neutrality and alkalinity, systems for preplating the bismuth membrane are generally of strong acidity; the concentration of the $Bi^{3+}$ is in the range of 5 mg/L to 200 mg/L; the electroplating voltage is in the range of −0.5V to 1.2V; the electroplating time is about 1 min to-8 min; and stirring is carried out at the same time.

2. A synchronous bismuth membrane plating method: the $Bi^{3+}$ solution with certain concentration is added in the solution to be detected; $Bi^{3+}$ in the solution to be detected and a sample to be detected are synchronously deposited on the surface of the working electrode in an electroplating process; the concentration of the $Bi^{3+}$ is in the range of 400-1000 µg/L; and generally, an acid buffer system is used as a medium.

Compared with a synchronous bismuth plating method, the bismuth membrane preplating method is complicated in operation and takes more time, and the electrode reproducibility of preplating a bismuth membrane is inferior to the electrode reproducibility of the synchronous plated bismuth membrane. The synchronous bismuth membrane plating method is adopted in the method provided by the present invention for forming the bismuth membrane on the working electrode.

Figure 8:
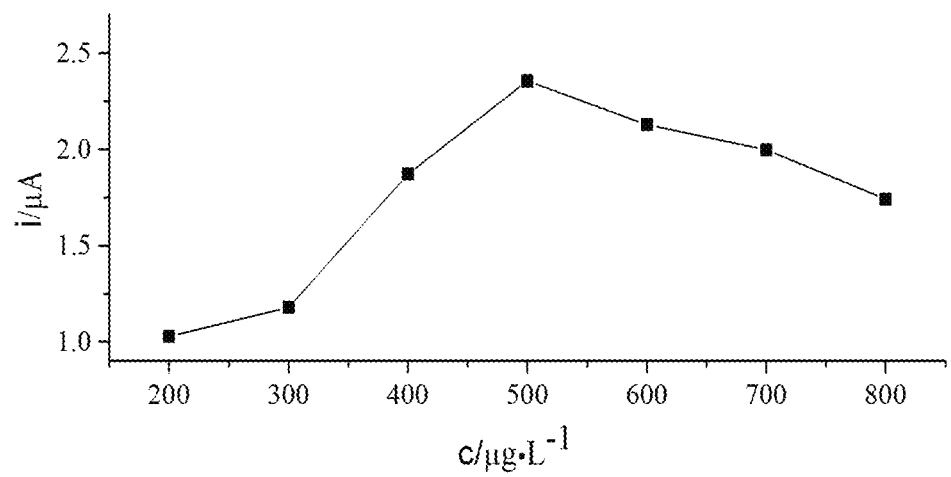
FIG. 8 is a $Pb^{2+}$ stripping peak current line graph at different $Bi^{3+}$ concentrations.

The thickness of the bismuth film is determined directly by the concentration of $Bi^{3+}$ in the solution to be detected. The lower the concentration of $Bi^{3+}$ is, the thinner a plated bismuth film is and the higher the concentration of electrodeposition heavy metals in the bismuth film is. As the stripping is relatively complete in the stripping scanning phase, the sensitivity is improved; if the concentration of $Bi^{3+}$ is too low, the formation of the bismuth film will not be compact and uniform enough and the reproducibility will be relatively poor; if the concentration of $Bi^{3+}$ is too high, the bismuth film will tend to be thick, and the reproducibility will become better, but the detection sensitivity will decrease. FIG. 8 is a diagram showing the stripping peak currents of $Pb^{2+}$ solution with a concentration of 40 µg/L under different $Bi^{3+}$ concentrations. The results show that in a lead standard solution with $Bi^{3+}$ concentration being 500 µg/L, the lead stripping peak has the biggest peak current and a better peak shape; with the increase of the $Bi^{3+}$ concentration, the stripping peak currents fall significantly. Therefore, in the implementation of the method of the present invention, the optimal $Bi^{3+}$ concentration in a solution to be detected is 500 µg/L.

Figure 9:
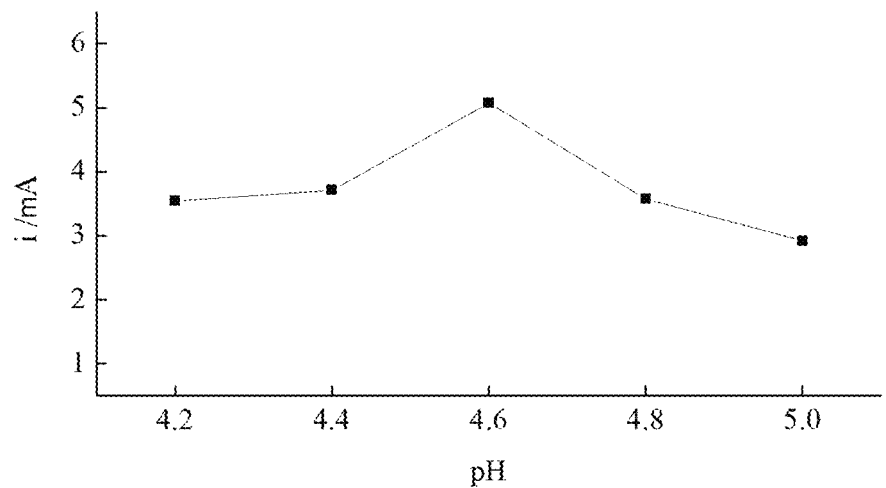
FIG. 9 is a $Pb^{2+}$ stripping peak current line graph at different pHs of a solution to be detected.

In the aforementioned basic technical scheme, the acidic base solution is added into the heavy metal ion solution to be detected to form an acidic buffer system required by the synchronous plating of the bismuth film. The base solution may be acetic acid-sodium acetate (NaAc—HAc) solution with a concentration of 0.1 mol/L, and the pH value of the solution to be detected is adjusted through the added amount of the NaAc-HAc solution. In the detection process, the pH value of the acidic buffer system in the solution to be detected can affect a stripping peak current signal of the detection. Selecting the best pH value of the buffer system can optimize the implementation of the application method of the present invention. FIG. 9 is a diagram showing the stripping peak currents of $Pb^{2+}$ solution with a concentration of 40 µg/L under different pH values of the solution to be detected. The results show that with the gradual increase of the pH value of the solution to be detected, the peak current of the $Pb^{2+}$ stripping peak increases gradually; when the pH value is equal to 4.6, the peak current of the lead ion stripping peak reaches a maximum value; with the further increase of the pH value, the stripping peak current decreases gradually. Therefore, in the implementation of the method of the present invention, the optimal pH value of the solution to be detected is 4.6.

The enrichment process is the first step of ASV detection in the aforementioned basic technical scheme and is realized through pre-electrolysis. The pre-electrolysis can be divided into two kinds: complete electrodeposition (stoichiometry) and partial electrodeposition (non-stoichiometry). The complete electrodeposition means that detected substances in a solution are completely electrolytically deposited on the working electrode. This method has relatively high sensitivity, but consumes a relatively long time. For sample solutions small in volume, the working electrode with a large area can be adopted so that all the substances to be detected can be electrolytically deposited within a certain time; the partial electrodeposition means that a certain proportion of substances to be detected are electrolytically deposited on the working electrode every time. This electrodeposition method is time-saving and has certain precision, which is the most commonly used enrichment method presently.

In the aforesaid basic technical scheme, the pre-electrolysis is carried out in the micro-channel of the detection device of the present invention. After reduction reaction occurs on the working electrode, the metal cations to be detected in the solution to be detected crystallize on the electrode surface. Generally, the electrocrystallization process has the following several steps:

1, liquid phase mass transfer: metal ions in the electrolytic cell migrate to the electrode surface;

2, preposed transformation: the metal ions react chemically on the electrode surface;

3, charge transfer: the metal ions are reduced into metal atoms to form crystal nuclei;

4, electrocrystallization: the metal atoms on the electrode diffuse along the electrode surface and enter crystal lattices, thereby forming crystals.

In the aforesaid basic technical scheme, the pre-electrolysis is carried out under the condition that the solution to be detected is in the flowing state. Driven by the peristaltic pump, the solution to be detected containing heavy metal ions flows continuously through the micro-channel; the flow can affect the flowing pattern of the solution and the update frequency of a detection area, and the flow is regulated through changing the rotation speed of the peristaltic pump and using pipes of different diameters; due to the flowing of the solution to be detected, the surface of the working electrode contacts a fresh solution with the highest concentration of metal ions all the time, without the need to await spreading, thereby effectively improving the efficiency of the pre-electrolysis enrichment.

In theory, metal ions are capable of depositing on a cathode so long as the metal ions can obtain certain overpotential; however, in the practical case, many other cations exist in the solution to be detected and can also be reduced by the cathode. At the same time, hydrogen ions in the solution can also participate in the reaction and form competition against the metal ions. Accordingly, the enrichment voltage in the enrichment process is a very important reaction condition. In the medium, the pre-enrichment voltage of stripping analysis can be obtained from data of half-wave potential $E_{1/2}$, and generally, the potential greater than the half-wave potential by 0.3V to 0.6V is adopted. The test indicates that if the concentration voltage is too close to the peak-out potential, the stripping current will be unstable, which causes influences on the reproducibility of the stripping current. While several ions are subjected to stripping analysis, the enrichment voltage is taken based on an element with the most negative peak potential; and in the embodiment of the present invention, the Pb is taken as the reference. Overhigh enrichment voltage can accelerate the deposition speed, but can also generate interference easily, in particular, hydrogen (H) in the solution to be detected can also separate out from the surface of the electrode, which directly affects the test result, so that the selection of the proper enrichment voltage may achieve the purpose of suppressing interferences.

Figure 10:
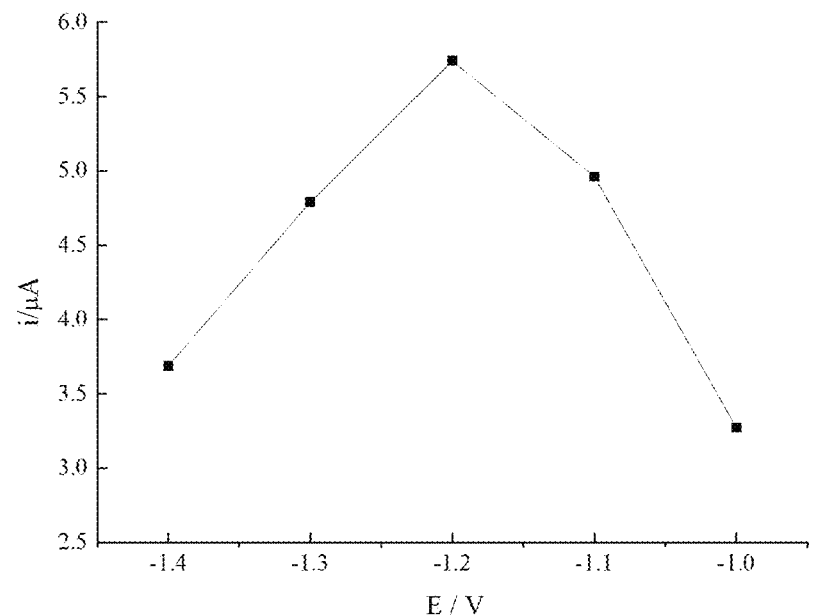
FIG. 10 is a $Pb^{2+}$ stripping peak current line graph at different enrichment voltages.

As shown in FIG. 10, when the $Pb^{2+}$ solution of 40 μg/L is subjected to the detection of the peak current of the stripping peak, the result shows that when the enrichment voltage is smaller than −1.2V, the peak current tends to increase; when the concentration voltage is greater than −1.2V, the peak current tends to decrease, and the peak potential shifts towards the negative direction; when the peak current is −1.2V, the peak current is the maximum, and the peak shape is the best. In order to guarantee the better peak shape and the greater peak current and prevent the interferences of stripping of other ions on Pb when the potential is relatively negative, the optimal enrichment voltage is −1.2V in the implementation of the method provided by the invention.

Figure 11:
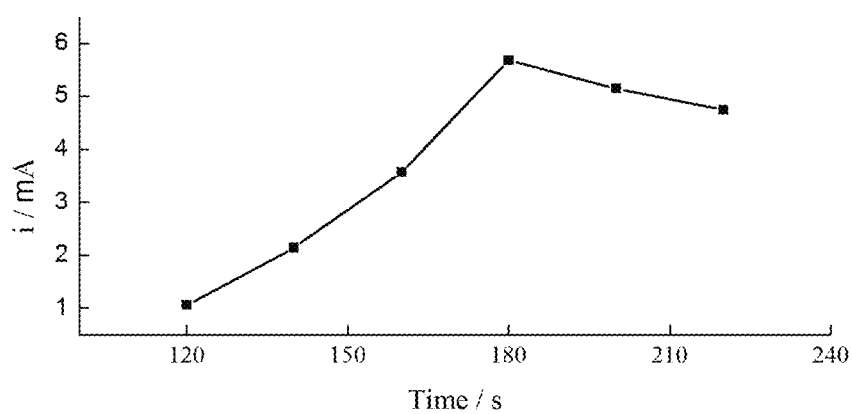
FIG. 11 is a $Pb^{2+}$ stripping peak current line graph at different enrichment time.

Besides the enrichment voltage, the enrichment time also has influence on the stripping peak current. As the amount of the metal Bi enriched on the working electrode is in direct proportion to the enrichment time within certain time, metal Bi will be in the approximately saturated state after certain time, so that reincreasing of the enrichment time will not increase the stripping peak current, instead, the metal Pb diffusing in a bismuth membrane may penetrate into the bismuth membrane with difficulty in stripping, and consequently, the stripping peak current decreases. After pre-electrolysis of the enrichment process, the driving for enabling the solution to be detected to flow needs to be stopped; after the detection system stands for some time, the heavy metal enriched on the working electrode is homogeneously diffuses on the surface of the bismuth membrane so as to generate an alloy-like effect, so that the stripping peak with good peak shape is obtained while stripping is scanned. During standing, the voltage on the working electrode needs to be kept constant, otherwise, the metal enriched on the surface of the bismuth membrane can not diffuse uniformly, which influences the peak shape of the stripping peak. The standing voltage is kept constant, different standing time for detection are selected, and a result shows that the peak current is enhanced gradually along with the prolongation of the standing time till reaching the stable state finally. As too long standing time will affect the factors such as the detection speed, the optimum standing time is selected as 60 s. As shown in FIG. 11, when the $Pb^{2+}$ solution of 40 μg/L is subjected to the detection of the peak current of the stripping peak under different concentration time, the enrichment time is selected within 120 s to 220 s and comprises the standing time after pre-electrolysis; and the enrichment time is preset as 60 s. The result shows that when the enrichment time is shorter than 180 s, the peak current gradually increases along with the increment of the enrichment time; when the enrichment time is longer than 180 s, the peak current starts to gradually decrease. Therefore, in the implementation of the method provided by the present invention, the optimum enrichment time is determined to be 180 s which corresponds to the highest point of the stripping peak current, wherein the standing time is 60 s.

Generally, the stripping process of ASV detection may also be divided into two modes: the partial stripping and the complete stripping. In the actual implementation, the stripping mode is selected based on the type of electrodes used and the features of the electrode reaction. When the traditional hanging mercury electrode is adopted as the working electrode, the enriched heavy metals to be detected are uniformly distributed in various parts of a mercury drop in the form of amalgam. As the speed of voltage scanning is fast, the stripping has to rely on the spreading of internal substances to be detected to the surface of the working electrode so as to continue to proceed. As being proportional to the concentration of the metal substances to be detected in the amalgam, its peak current ip is proportional to the initial concentration of the heavy metal ions to be detected in the solution to be detected. Therefore, the partial stripping mode can be adopted; when the solid electrode or the membrane electrode with a very small thickness is used, the complete stripping mode must be adopted. This is because the mercury film or bismuth film is relatively thin on the surface of such a working electrode in the enrichment process; during the stripping, the metals to be detected in the film are stripped rapidly from the electrode surface, defying the establishment of the limiting diffusion current, and the stripping peak current ip is proportional to the total amount of the substances to be detected in the film on the working electrode. The detection device of the present invention is the all-solid-state card electrode, and the complete stripping mode is adopted for ASV detection.

Figure 12A:
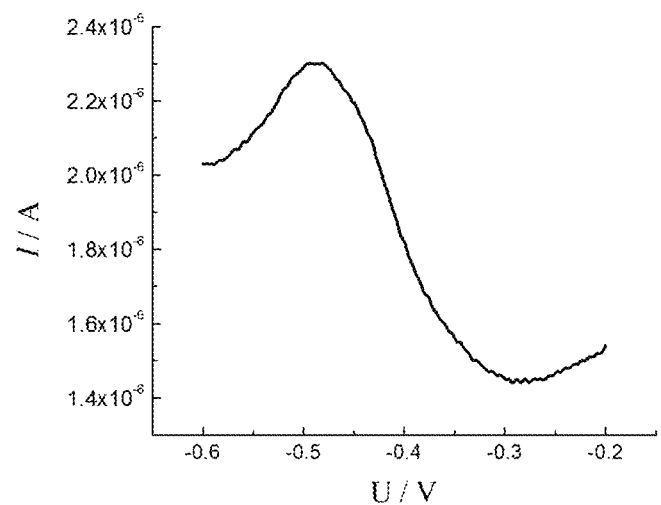
FIG. 12A is a stripping voltammetry curve of $Cd^{2+}$ with the same concentration in three potential scanning modes, it shows square wave scanning.
Figure 12B:
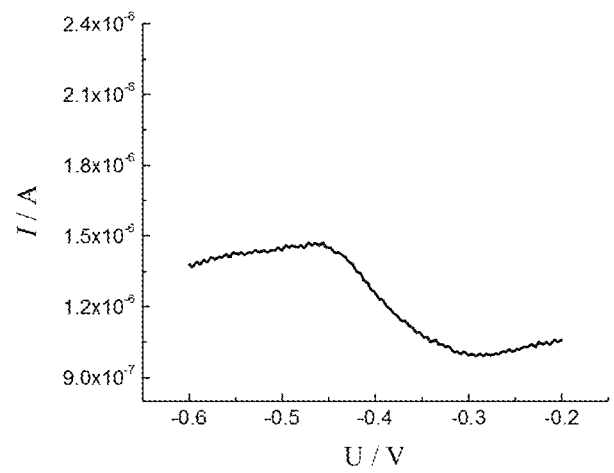
FIG. 12B is a stripping voltammetry curve of $Cd^{2+}$ with the same concentration in three potential scanning modes, it shows differential pulse scanning.
Figure 12C:
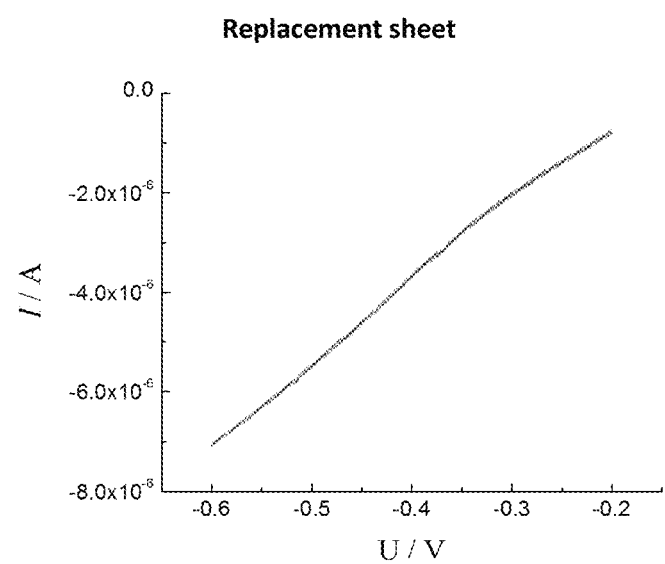
FIG. 12C is a stripping voltammetry curve of $Cd^{2+}$ with the same concentration in three potential scanning modes, it shows linear scanning.

Generally, the potential scanning method of the ASV stripping process includes the differential pulse scanning, the square wave scanning, the linear scanning, etc. Current signals and background currents obtained through different scanning methods are various, and therefore there are differences in the sensitivity and the detection limit of the detected results. FIGS. 12a, 12b and 12c record respectively the stripping voltammetry curves of $Cd^{2+}$ solution with a concentration of 50 μg/L under three different scanning methods. As can be seen from the figures, when $Cd^{2+}$ having the identical concentration is detected, the stripping current of the square wave scanning is biggest, with a low background noise; the second is the signal of the differential pulse voltammetry; however, by using the linear scanning voltammetry, there is almost no significant peak-shaped response signal; meanwhile, in the aspect of the experiment operation, the square wave scanning voltammetry has a short scanning time, stripped oxygen of which can be discharged without the pumping-in of nitrogen, and therefore, the operation is relatively convenient. Consequently, during the stripping in the detection process of the present invention, the square wave scanning is taken as the best mode, and the used detection method is the square wave ASV (SWASV). All the stripping peak current data of the preferred embodiment described above is obtained through SWASV.

Figure 13:
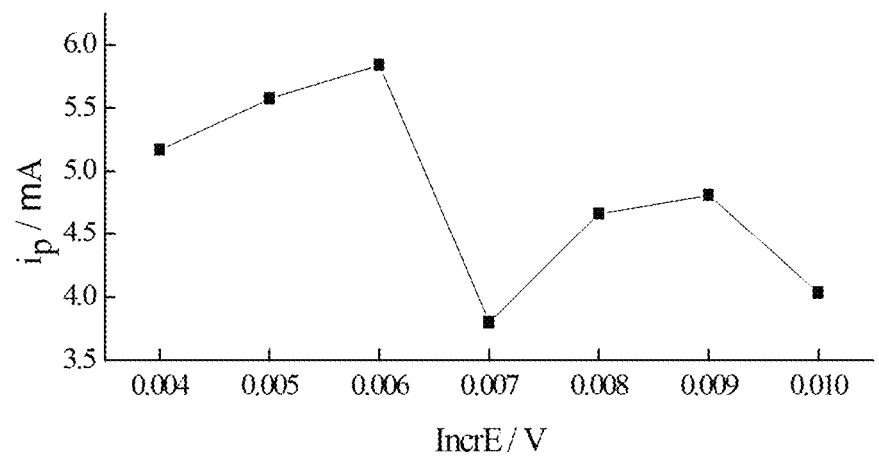
FIG. 13 is a stripping peak current line graph of $Pb^{2+}$ in different potential increments.

The scanning potential increment exerts an influence on the stripping peak current. SWASV is adopted for the detection of $Pb^{2+}$ solution with a concentration of 40 μg/L under multiple potential increments ranging from 0.004V to 0.01 V, and the values of the stripping peak current are shown in FIG. 13. The detection results show that when the potential increment is less than 0.006V, the peak current tends to increase as the potential increment increases; when the potential increment is 0.006V, the peak current reaches the maximum value; when the potential increment is larger than 0.006V, the peak current tends to decrease as a whole with the increase of the potential increment; in addition, it is found after repeated detection that when the potential increment is larger than 0.006V, the current peak form in the stripping voltammetry curve is poor, and the peaks become asymmetric; as the peak shape and background of the potential increment which is 0.006V are somewhat poorer than those of the potential increment which is 0.005V, in the implementation of the method of the present invention, the potential increment of 0.005V is optimal after the overall consideration of the peak current and peak shapes.

The basic technical solution of the application of the detection device of the present invention to the detection of heavy metal ions is as follows:

the detection device uses the structures in the previously described technical solution that are shown in FIGS. 3-6, wherein:

the working electrode 121 uses the silver-carbon electrode, the counter electrode 122 uses the silver electrode, and the reference electrode 123 uses the silver-silver chloride electrode. The three electrodes are all in the shape of a square; the micro-channel 22 is the saddle-shaped cavity whose thickness is 0.9 mm; the connections of the liquid inlet pipeline 221 and the liquid outlet pipeline 222 are at the two top ends of the saddle-shaped cavity, the direction of each pipe orifice is tangent to the cavity edge of the connection points, and the inner diameter is 0.83 mm, which is slightly smaller than the thickness of the micro-channel;

the detection process is carried out based on the steps of the basic technical solution of the present invention described previously, wherein:

the concentration of $Bi^{2+}$ in the solution to be detected is 500 μg/L, the buffer solution employs the NaAc—HAc base solution with a concentration of 0.1 mol/L, and the pH value of the solution to be detected is set to be 4.6; the enrichment voltage is set to be −1.2V, the enrichment time is set to be 180 s (which includes 60 s of standing), and the flow is set to be 1.2 mL/min. In the stripping process, the square wave potential scanning is adopted, and the parameters of the electrochemical analysis work station are set as follows: the initial potential is −0.9V, the final potential is −0.2V, the potential increment is 0.005V, the amplitude is 0.025V, the frequency is 25 Hz, the quiescent time is 2 s, and the sensitivity is 1.00e-04 A/V.

Figure 14:
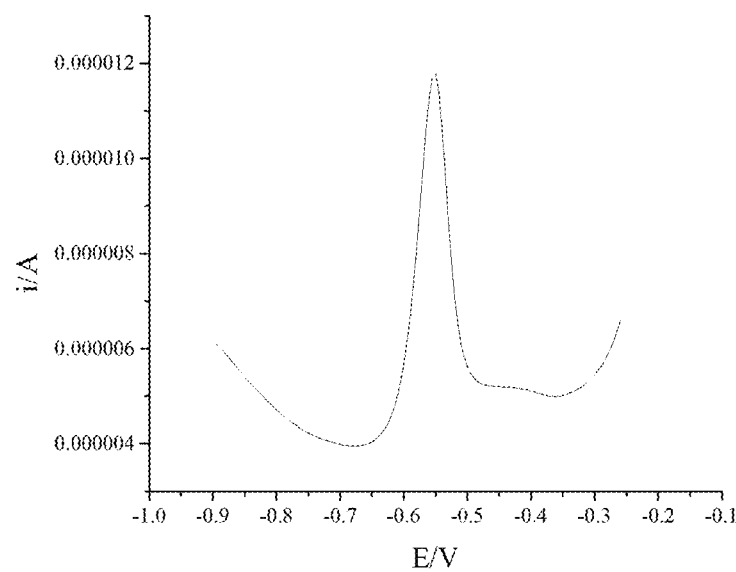
FIG. 14 is a stripping voltammetry curve generated when the detection device in the present invention detects single $Pb^{2+}$.
Figure 15:
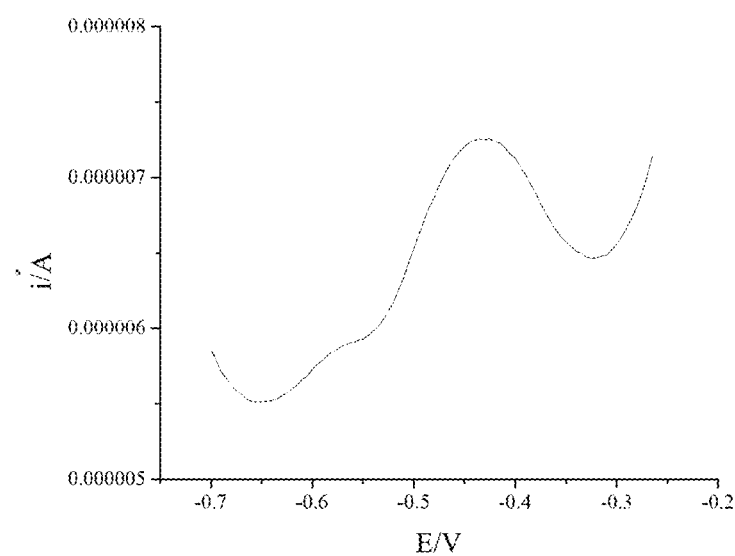
FIG. 15 is a stripping voltammetry curve obtained when the detection device in the present invention detects single $Cd^{2+}$.
Figure 16:
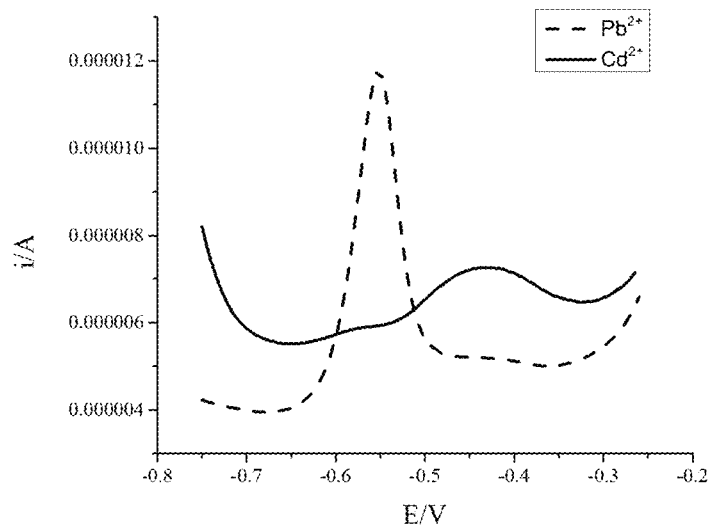
FIG. 16 is a combined diagram of the stripping voltammetry curves in FIGS. 14 and 15.

The stripping voltammetry curve obtained from the detection of the single heavy metal ion $Pb^{2+}$ with a concentration of 50 μg/L is shown in FIG. 14; the stripping voltammetry curve obtained from the detection of the single heavy metal ion $Cd^{2+}$ with a concentration of 50 μg/L is shown in FIG. 15; and FIG. 16 is a combined diagram of the stripping voltammetry curves in FIGS. 14 and 15 described above.

Figure 17:
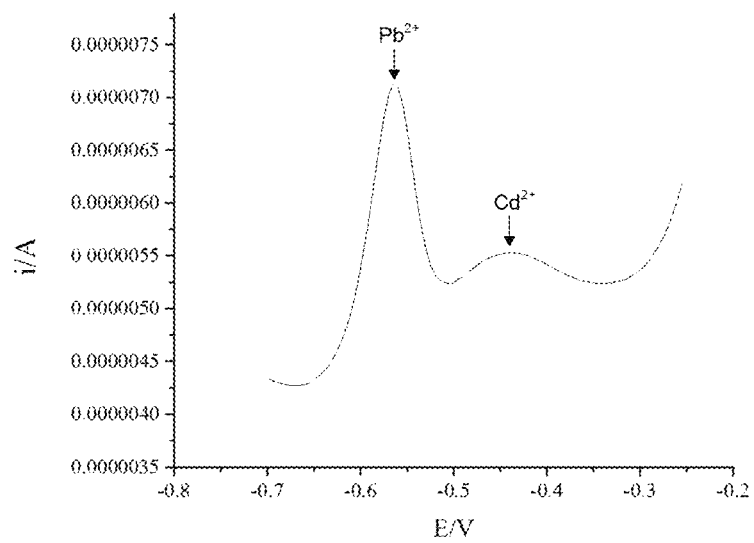
FIG. 17 is a stripping voltammetry curve obtained when the detection device in the present invention simultaneously detects $Pb^{2+}$ and $Cd^{2+}$.

The stripping voltammetry curves obtained from the simultaneous detection of $Pb^{2+}$ and $Cd^{2+}$ which have the same concentration of 40 μg/L are shown in FIG. 17, and have two peak currents corresponding to $Pb^{2+}$ and $Cd^{2+}$ respectively.

Figure 18:
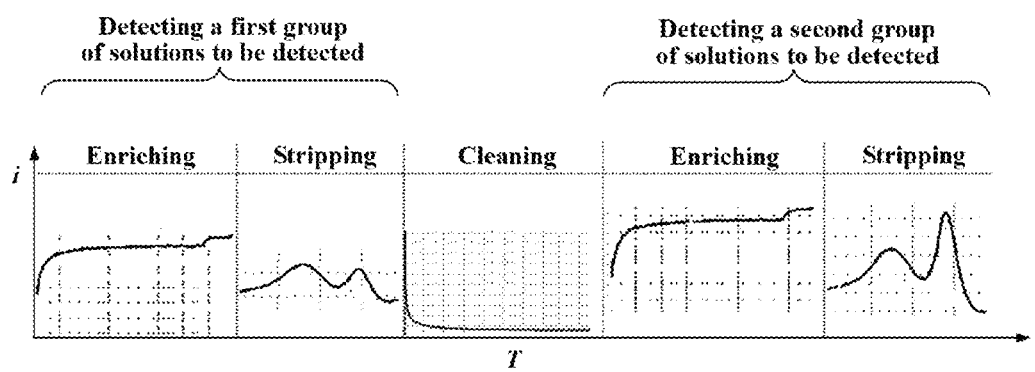
FIG. 18 is a schematic flow diagram obtained when the detection device in the present invention continuously detects two groups of solutions to be detected.

The process for continuously detecting multiple groups of heavy metal ion solutions by employing the above-mentioned detection device is shown in FIG. 18. After the detection process of the first group of solutions to be detected is completed, the simple cleaning is carried out, then the solution to be detected which is prepared by the second group of solutions to be detected can be introduced into the micro-channel for the second round of detection. During this process, signals are continuously collected by the electrochemical analysis work station. FIG. 18 is a schematic drawing showing the current changing with time in the whole continuous detection process.

Figure 19A:
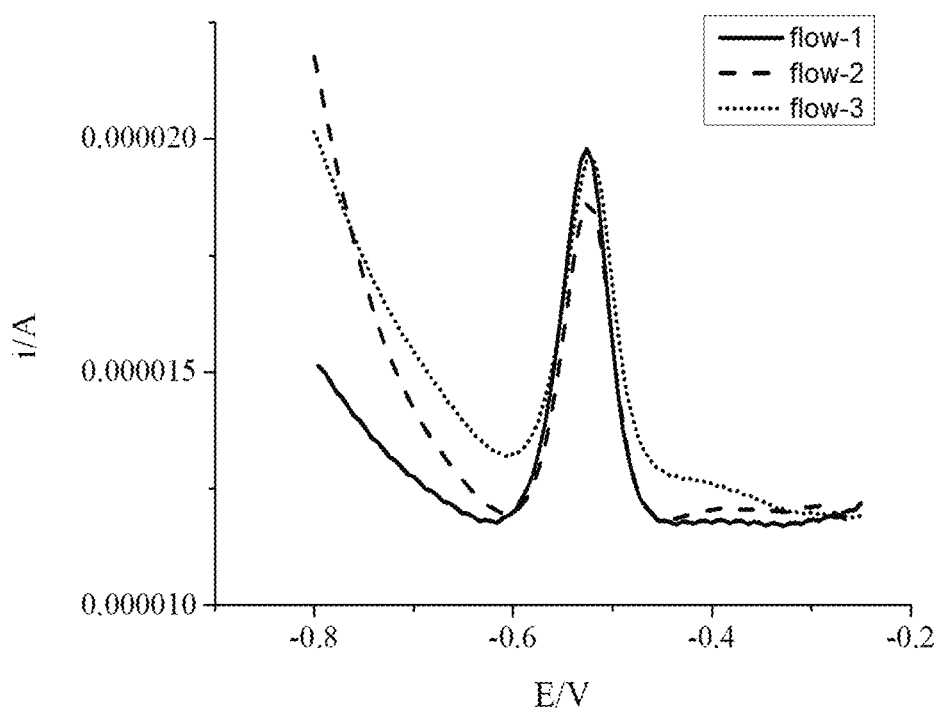
FIG. 19A is a comparison diagram of stripping voltammetry curves obtained by repeatedly detecting a $Pb^{2+}$ sample, it shows using the detection device and method in the present invention.
Figure 19B:
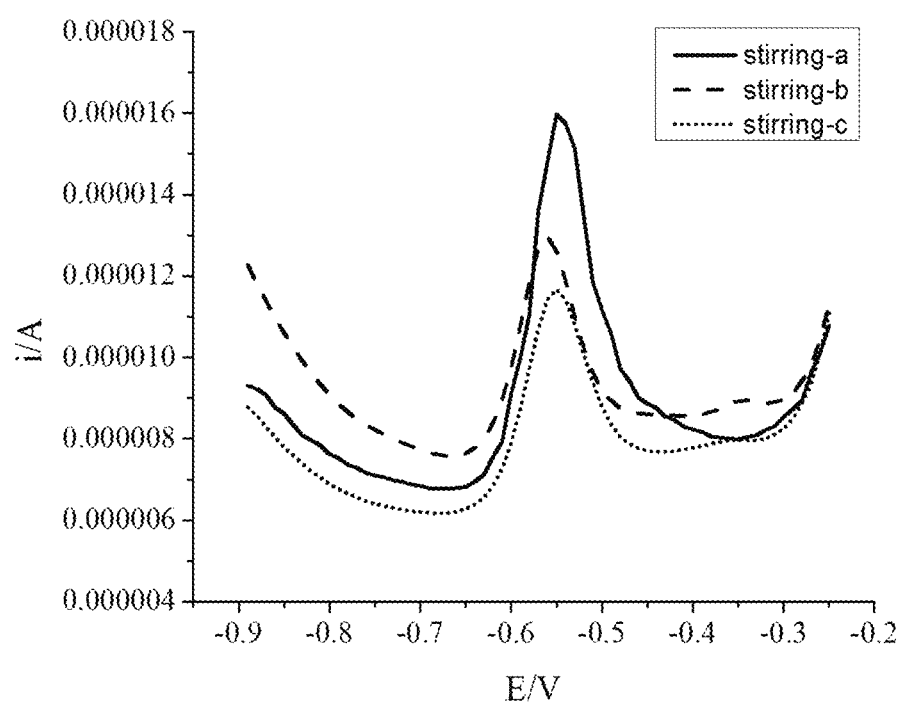
FIG. 19B is a comparison diagram of stripping voltammetry curves obtained by repeatedly detecting a $Pb^{2+}$ sample, it shows using a traditional ASV detection mode.

The detection device in the above-mentioned basic technical solution of the detection of heavy metal ions is used for repeatedly detecting multiple solution samples of heavy metal ions to be detected which have the same concentration, thereby examining the repeatability of the technical solution of the present invention. The detection parameters are set as follows:

the concentration of $Bi^{3+}$ in the solution to be detected is 400 μg/L, the buffer solution employs the NaAc—Hac base solution with a concentration of 0.1 mol/L, and the pH value of the solution to be detected is set to be 4.6; the enrichment voltage is set to be −1.2V, the enrichment time is set to be 180 s (which includes 60 s of standing), and the flow is set to be 1.2 mL/min. In a stripping process, the initial potential is −0.9V, the final potential is −0.2V, the potential increment is 0.006V, the amplitude is 0.025V, the frequency is 30 Hz, the quiescent time is 2 s, and the sensitivity is 1.00e-04 A/V. The three stripping voltammetry curves shown in FIG. 19 are obtained after repeatedly detecting the $Pb^{2+}$ with a concentration of 60 μg/L for three times.

For comparison, under the condition that the detection parameters are basically identical, the traditional mode ASV is used for repeatedly detecting $Pb^{2+}$ with the above-mentioned concentration. The detection is carried out in a beaker.

In the enrichment process, stirring is carried out, and the three stripping voltammetry curves shown in FIG. 20 are obtained. It can be seen from the comparison between FIG. 19 and FIG. 20 that the reproducibility of the technical solution of the present invention in detection is obviously superior to that of the traditional mode of ASV detection.

Figure 20A:
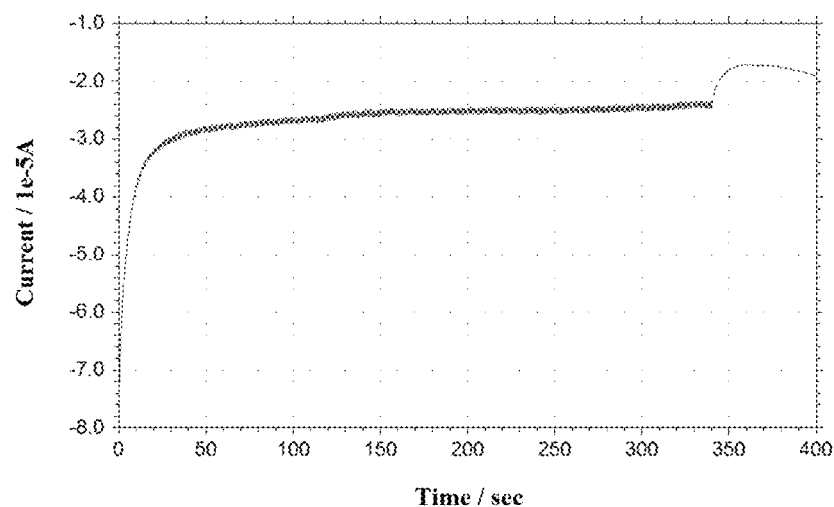
FIG. 20A is an enrichment current-time curve of $Pb^{2+}$ sample pre-electrolysis which is obtained by using the detection device and method in the present invention.
Figure 20B:
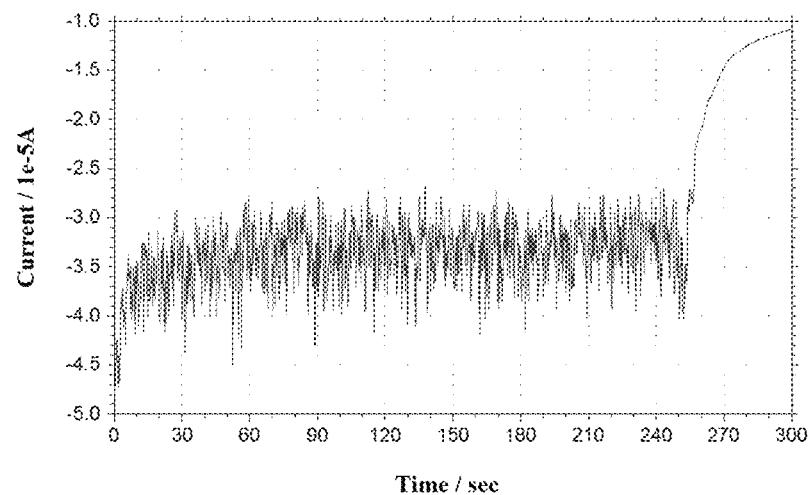
FIG. 20B is an enrichment current-time curve of $Pb^{2+}$ sample pre-electrolysis which is obtained by using a traditional ASV detection mode.

The detection device in the above-mentioned basic technical solution of the detection of heavy metal ions is employed to carry out pre-electrolysis on a $Pb^{2+}$ solution sample with a concentration of 60 μg/L, and the changes of the accumulated current corresponding to those of time are recorded, wherein the concentration of $Bi^{3+}$ in the solution to be detected is 500 μg/L, the buffer solution employs the NaAc—Hac base solution with a concentration of 0.1 mol/L, and the pH value of the solution to be detected is set to be 4.6; the enrichment voltage is set to be −1.2V, the enrichment time is set to be 300 s, and the flow is set to be 1.2 mL/min; after that, the enrichment current-time curve shown in FIG. 20a is obtained. As comparison, under the condition that the detection parameters are basically identical, the traditional three-electrode system is used for carrying out pre-electrolysis on a $Pb^{2+}$ solution sample in a beaker. The whole pre-electrolysis process is accompanied with stirring, and then the enrichment current-time curve shown in FIG. 20b is obtained. From the comparison between the above-mentioned two figures, a large number of irregular burrs are generated in the accumulated current-time curve of the traditional three-electrode system, while the accumulated current-time curve obtained by the detection device and the method of the present invention is rather smooth, which further indicates that the use of ASV detection of the technical solution of the present invention leads to a good reproducibility.

The influence of the structure and size of the detection device of the present invention on detection effects is analyzed by the following experiments and simulated calculations, thereby further optimizing the technical solution of the present invention.

The micro-channel in the detection device of the present invention may have multiple shapes, wherein the saddle shape and the rectangular shape are most representative. The shape and the pipeline connection manners of the micro channel are optimized by comparing and analyzing the working conditions of a saddle-shaped micro channel and a rectangular micro channel.

Figures 21A, 21B, 21C:
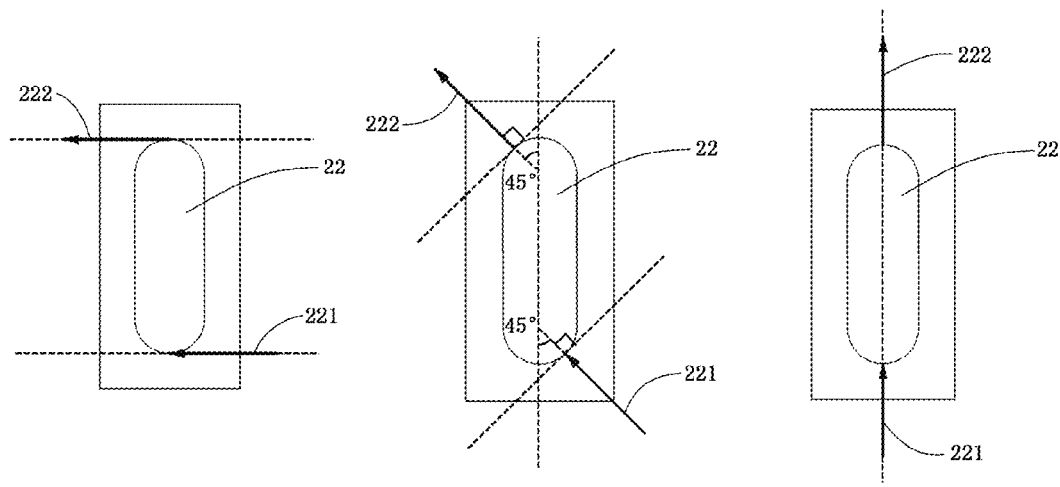
FIG. 21A is a schematic diagram of three connection modes between a saddle-shaped micro-channel and a pipe, it shows a tangential connection.
FIG. 21B is a schematic diagram of three connection modes between a saddle-shaped micro-channel and a pipe, it shows a normal connection of 45°.
FIG. 21C is a schematic diagram of three connection modes between a saddle-shaped micro-channel and a pipe, it shows a through connection.
Figure 22:
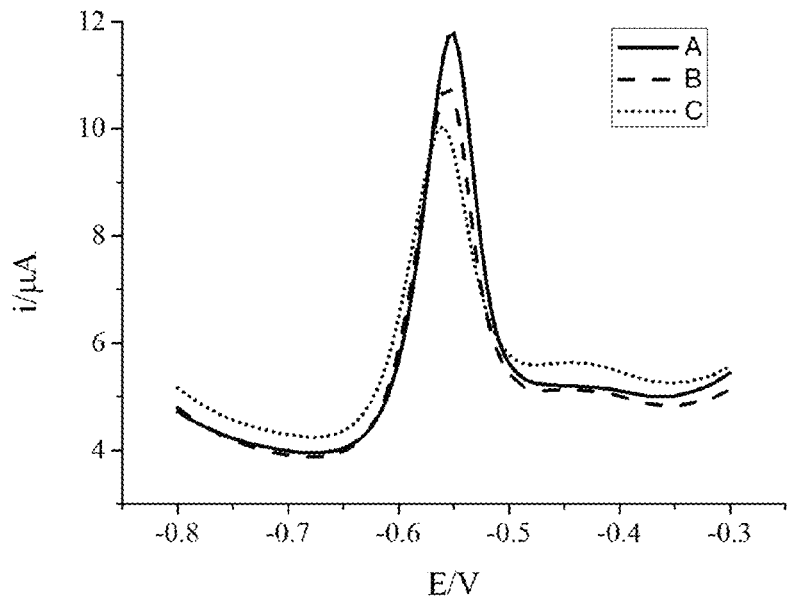
FIG. 22 is a comparison diagram of stripping voltammetry curves obtained by detecting a $Pb^{2+}$ sample in the three connection modes shown in FIG. 21.

With reference to the detection process of single heavy metal ion $Pb^{2+}$ in the above-mentioned technical solution, a saddle-shaped micro channel 22 is used in the detection device, the connection among a liquid inlet pipeline 221, a liquid outlet pipeline 222 and the micro channel 22 is shown in FIGS. 21a, 21b and 21c; and three manners including a tangent line manner, a 45-degree normal manner, and a straight through manner are adopted respectively; a $Pb^{2+}$ sample with the concentration of 60 μg/L is detected when other detection conditions are unchanged so as to obtain stripping voltammetry curves under three different connection manners shown in FIG. 22; curves A, B and C in the figure respectively correspond to the tangent line manner, the 45-degree normal manner and the straight through manner. As shown in FIG. 22, for the saddle-shaped micro channel, the stripping peak current of the curve A is highest; the heavy metal ions to be detected flowing through a micro channel solution can be enriched on the surface of the working electrode under this connection manner; the stripping peak current of the curve B is lower than that of the curve A; the solution has similar flow field during flowing through the micro channel under the connection manners of the curve B and the curve A; however, the connection manner of the curve B enables the flow field of the solution to be relatively shorter, the enrichment time of the metal ions in the solution on the surface of the working electrode is short; and the stripping peak current is reduced; the stripping peak current of the curve C is lowest. Due to the straight through connection manner, the solution has a relatively high flow speed in the micro channel, so that the thickness of diffusion layers of the heavy metal ions to be detected in the solution can be reduced, and reactants have not enough time to deposit on the surface of the electrode. Therefore, when the micro channel of the detection device is saddle-shaped, the optimal connection manner between the pipeline and the micro channel is the tangent line connection manner shown in FIG. 21a.

Figures 23A, 23B, 23C:
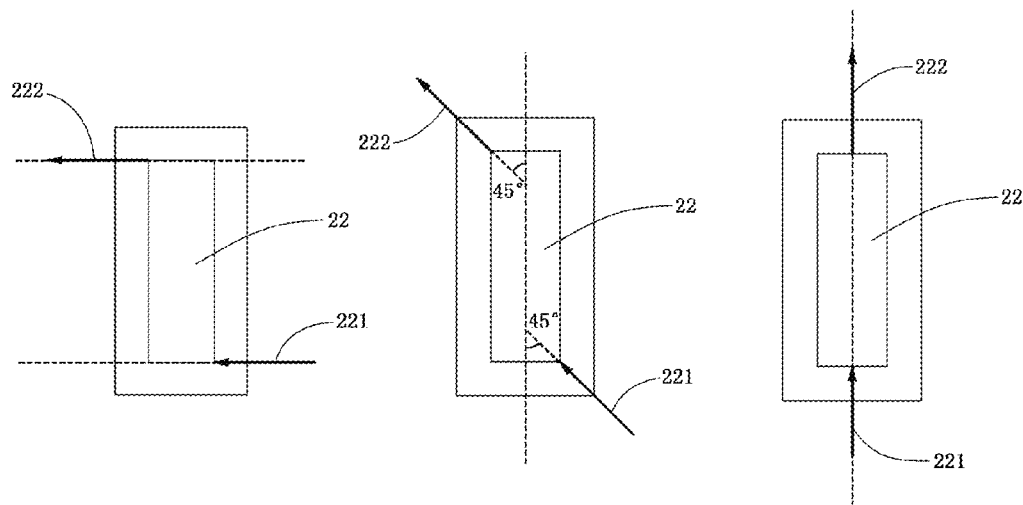
FIG. 23A is a schematic diagram of three connection modes between a rectangular micro-channel and a pipe, it shows a tangential connection.
FIG. 23B is a schematic diagram of three connection modes between a rectangular micro-channel and a pipe, it shows a directional connection of 45'.
FIG. 23C is a schematic diagram of three connection modes between a rectangular micro-channel and a pipe, it shows a through connection.
Figure 24:
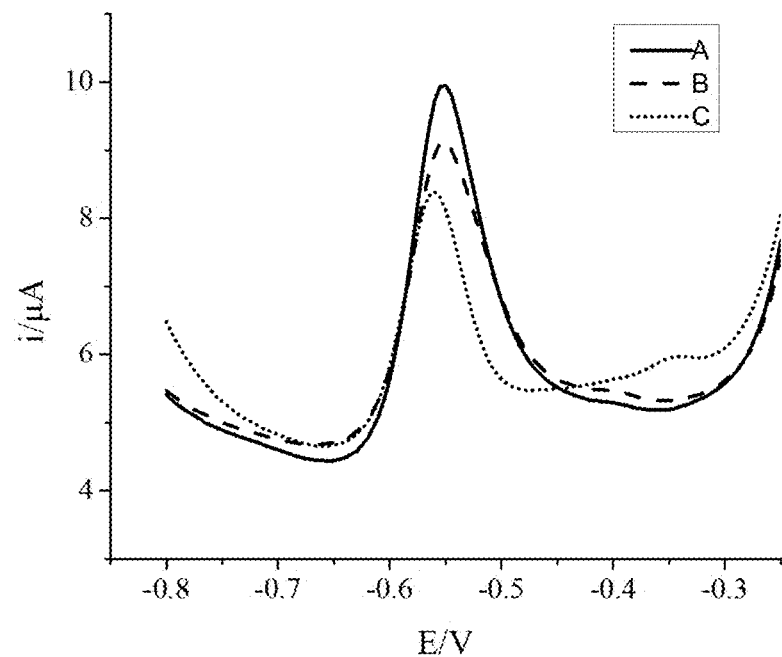
FIG. 24 is a comparison diagram of stripping voltammetry curves obtained by detecting a $Pb^{2+}$ sample in the three connection modes shown in FIG. 23.

With reference to the detection device and the parameter setting, a rectangular micro channel 22 is adopted; the connection among the liquid inlet pipeline 221, the liquid outlet pipeline 222 and the rectangular micro channel 22 is shown in FIGS. 23a, 23b and 23c; the connection manners comprise a tangent line manner, a 45-degree direction manner and a straight through manner; similarly, the $Pb^{2+}$ sample with the concentration of 60 μg/L is detected to obtain stripping voltammetry curves under three different connection manners shown in FIG. 24; the curves A, B and C in the figure respectively correspond to the tangent line manner, the 45-degree direction manner and the straight through manner. As shown in FIG. 24, the stripping peak current of the curve A is highest, the stripping peak current of the curve B takes second place, and the stripping peak current of the curve C is minimum, which is basically consistent with the comparison result of three curves in the case of the saddle-shaped micro channel; the principles are also basically same; however, by comparing the stripping voltammetry curves in FIGS. 22 and 24, it can be stripped that the stripping peak value in FIG. 22 is generally higher than that in FIG. 24, namely, the peak current of the saddle-shaped micro channel is higher than that of the rectangular micro channel, mainly because a dead angle of low flow speed at the corner of a rectangular cavity is large, and meanwhile, the regularization and concentration of the solution in a high-flow-speed area in the rectangular cavity are inferior to those of the solution in a saddle-shaped cavity. Therefore, the optimal micro-channel shape of the detection device is the saddle shape; the optimal pipeline connection mode is characterized in that the liquid inlet pipeline and the liquid outlet pipeline are connected to two top ends of the saddle-shaped cavity respectively; each pipeline orifice direction is tangent to the edge of the saddle-shaped cavity at a connection point.

In the detection device of the present invention, the thickness of the micro-channel and the flow rate of the solutions are important factors that affect the detection effect. The maximum range of the thickness of the micro-channel is 0.1 mm to 2.5 mm. However, too big micro-channel thickness would lead to excessive thickness of a diffusion layer of the solution, which is adverse to transmission of substances in the micro-channel; and too small micro-channel thickness would lead to too little quantity of the flowing solution, which is adverse to improvement of the total enrichment amount in unit time. Therefore, the thickness range of the micro-channel is further limited to 0.8 mm to 1.2 mm. The range of the inner diameter of the liquid inlet pipeline and the liquid outlet pipeline which are connected with the micro-channel is identical to that of the thickness of the micro-channel, but in the same detection device, the inner diameter of the pipelines is not bigger than the thickness of the micro-channel connected with the pipelines. In the detection process of the detection device, the flow rate of the solution is controlled by the peristaltic pump to be in a range of 0.01 m/s-0.3 mm/s in general. The faster the flow rate is, the thinner the thickness of the diffusion layer is. This is favorable for transmission of substances in the micro-channel, meanwhile the quantity of the solutions flowing through the electrodes is increased, the total quantity of substances to be detected increases, and the enrichment efficiency can be improved. However, if the flow rate is too fast, the substances in the solution to be detected would have no sufficient time to react on the electrodes, which would instead reduce the enrichment efficiency. Therefore, the range of the flow rate is further limited to be 0.02 m/s to 0.05 m/s.

When the diameter of the pipelines of the detection device is 0.8 mm to 1.2 mm and the flow rate of a fluid in the pipes is 0.02 m/s to 0.05 m/s, the viscosity μ of carrying currents is that $\mu \approx 1 \times 10^{-3}$ Pa·s, and when the density is close to that of water, the Reynolds number Re of the fluid in the pipelines of the detection device is about 100, and laminar flow is the main fluid pattern of the fluid in the pipelines. When a diffusion coefficient $\alpha \approx 1 \times 10^{-9}$ m$^2$/s, a Pukeleite number Pe acquired through further calculation is that: $4 < \log Pe < 5$ and meanwhile $3.17 < \log L/\alpha < 3.70$, indicating that in the embodiment of the invention, mass transfer of the fluid in the pipelines of the detection device occurs in a transition region at the border of a convection area and a Taylor dispersion area, with diffusion serving as the main drive force of mass transfer.

To further optimally design the micro-channel in the detection device, COMSOL Multiphysics software is used, and an FEM (Finite Element Method) is adopted to carry out analog computation on the micro-channel. The COMSOL Multiphysics software is a kind of high-class numerical simulation software developed by the Sweden COMSOL company and is suitable to simulate various physical processes in the scientific and engineering fields. It is widely applied to scientific research and engineering calculations in various fields. Various FEM-based analog modules are set in the COMSOL Multiphysics software, which achieve analogue simulation of real physical phenomena by solving partial differential equations (single field) or partial differential equation sets (multi-fields). A chemical engineering module in the COMSOL Multiphysics is configured to simulate the detection device, and the module can simulate expansion interfaces in free media and porous media caused by convection, diffusion and migration of substances with different concentrations.

Regarding the fluid characteristics and the electrochemical reaction on the electrode surface in the technical solution of the invention, a Navier-Stokes equation (equation 1)

$$\rho\left(\frac{\partial u}{\partial t} + u \cdot \nabla u\right) = -\nabla p + \mu \nabla^2 u + f$$

and a convection diffusion equation (equation 2) are adopted $$\frac{\partial c}{\partial t} = D\nabla^2 c - u \cdot \nabla c$$

to solve substance viscosity and electrochemical activity respectively. In the above quotations, ρ represents fluid viscosity, μ represents kinematic viscosity, p represents pressure, u represents the flow rate of the fluid, f is external stress, D is the substance diffusion coefficient and c represents substance concentration.

The to-be-simulated micro-channel adopts the basic structure shown in FIGS. 4-6, the micro-channel 22 is saddle-shaped, the liquid inlet pipeline 221 and the liquid outlet pipeline 222 are connected at two top ends of a saddle-shaped cavity, and the pipeline orifice direction of each connection point is tangent to the edge of the cavity at the connection point.

Figure 25A:
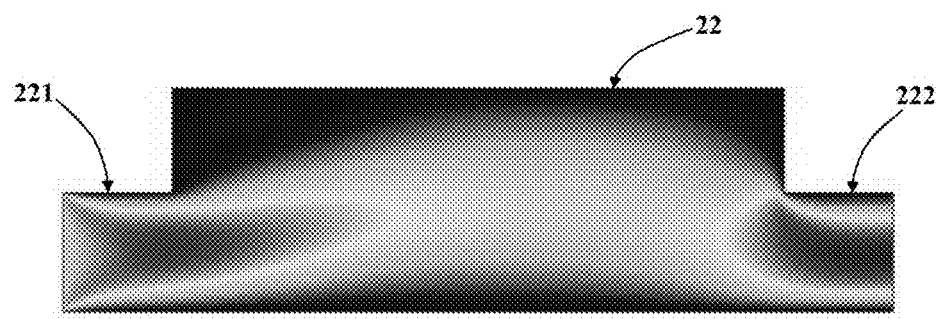
FIG. 25A is an analog flow field diagram of the saddle-shaped micro-channel shown in FIG. 4 to FIG. 6, which is a view in the D1 direction in FIG. 5.
Figure 25B:
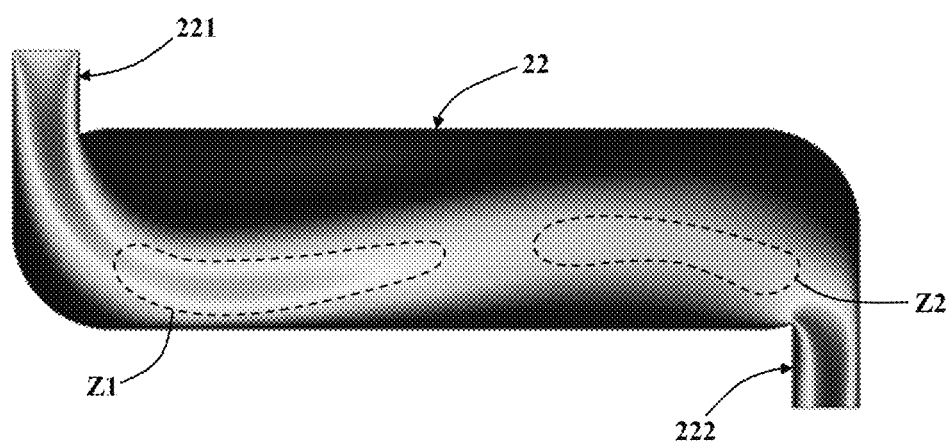
FIG. 25B is an analog flow field diagram of the saddle-shaped micro-channel shown in FIG. 4 to FIG. 6, which is a view in the D2 direction in FIG. 5.
Figure 26:
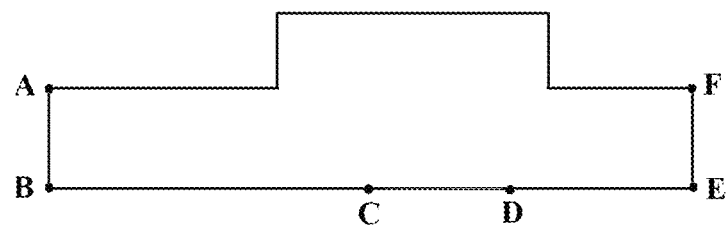
FIG. 26 is a schematic diagram of a computation master domain of analog computation.

Relevant parameters are input into the COMSOL 3.5a software for analog computation, through which the flow field diagram of the micro-channel 22 shown in FIGS. 25*a* and 25*b* is acquired. FIG. 26 shows the calculation primary domain during simulation, and the following Table 1 shows the initial value and the boundary condition when the calculation primary domain is calculated by using the above equation 1 and equation 2.

TABLE 1

| Interface | Equation 1 | Equation 2 | Initial value |
| --- | --- | --- | --- |
| AB | $u_x$ = 0.037 m/s | c = $c_0$ | $c_0$ = 0.00029 mol/m$^3$ |
| CD | No slip | c = 0 | |
| EF | p = 0 | Convective flux | |
| BC, DE, AF | No slip | Isolated/Symetrical | |

In the present invention, the micro-channel size and experimental parameters act as the stimulated representative conditions, and the representative values of the diffusion coefficient are selected according to publications; since the reference electrode and the counter electrode difficultly have an impact on electrochemistry at the same time, only the working electrode is considered in a calculation model.

Figure 27:
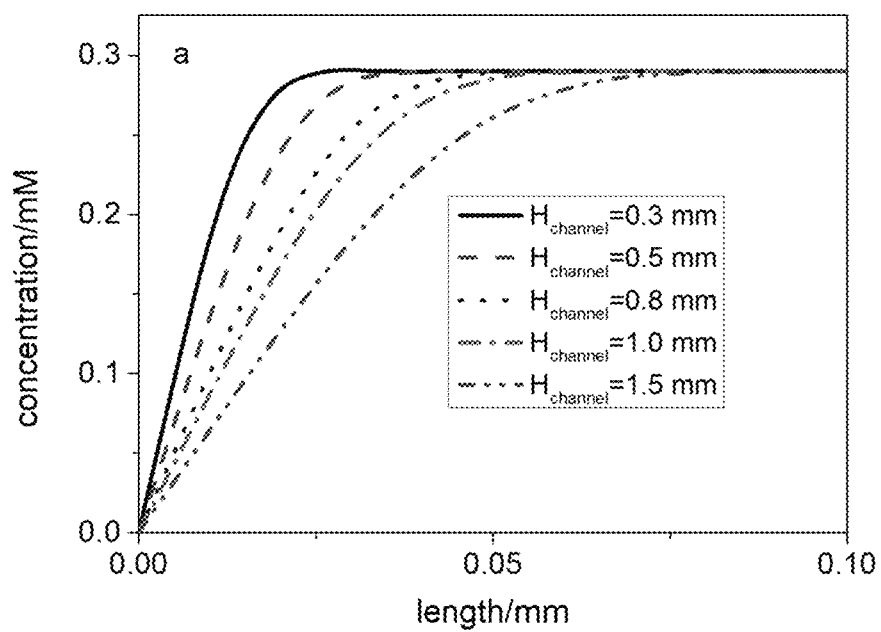
FIG. 27 is a comparison diagram of diffusion layer thickness of a flowing solution in different micro-channel thicknesses ($H_{channel}$) of analog computation.
Figure 28:
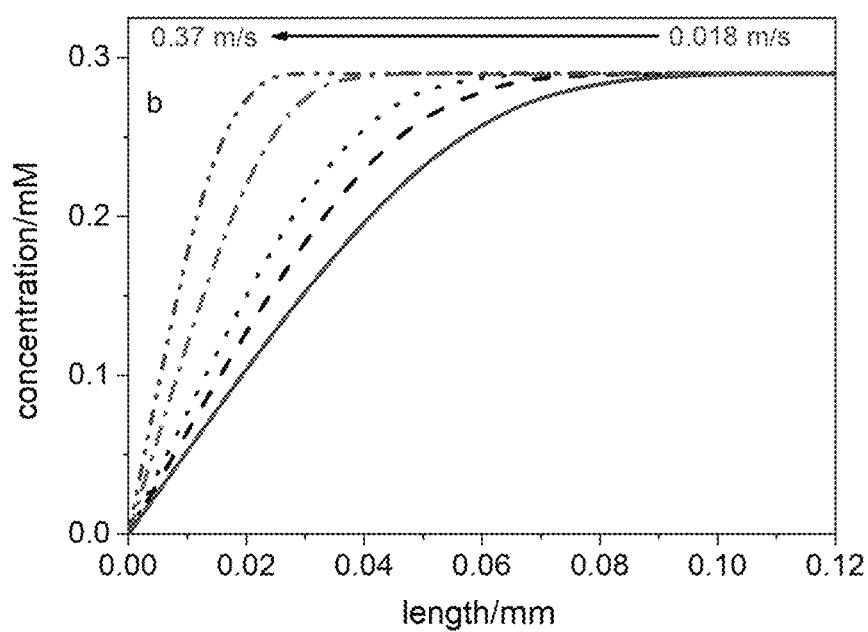
FIG. 28 is a comparison diagram of diffusion layer thicknesses of a flowing solution in a flow rate of analog computation.

The FEM simulation method is used; firstly the thicknesses of diffusion layers corresponding to different thicknesses of micro-channels are examined at the same flow rate, wherein the diffusion layer thickness being defined as the length of a change region from 0 to the bulk concentration: as shown in FIG. 27, when the thickness of the micro-channel $H_{channel}$ changes from 1.5 mm to 0.3 mm, the diffusion layer thickness is reduced from 100 μm to 27 μm; the influence of the flow rate on the thickness of the diffusion layer is then examined: as shown in FIG. 28, when the micro-channel thickness is fixed at 1.5 mm and the flow rate increases from 0.018 m/s to 0.37 m/s, the diffusion layer thickness is reduced from 120 μm to 30 μm. The simulation results show that both the micro-channel thickness and the pipeline flow rate can affect the diffusion layer thickness, wherein the flow rate plays a dominant role in the influence on the diffusion layer thickness; in case of a fixed micro-channel thickness for the detection device, adjusting the flow rate is used as a means of controlling the diffusion layer thickness.

Figure 29:
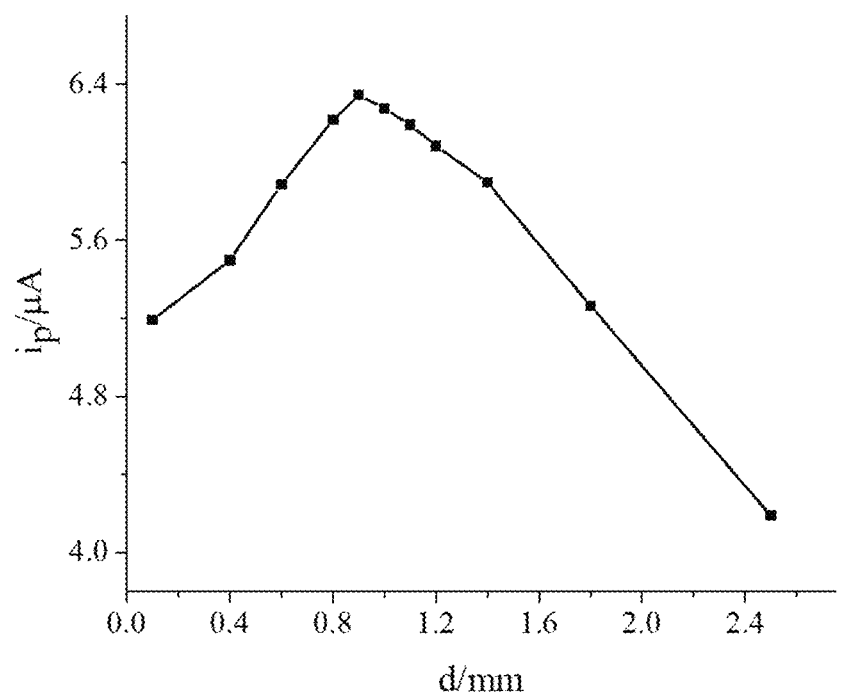
FIG. 29 is a stripping peak current line of $Pb^{2+}$ in different micro-channel thicknesses.
Figure 30:
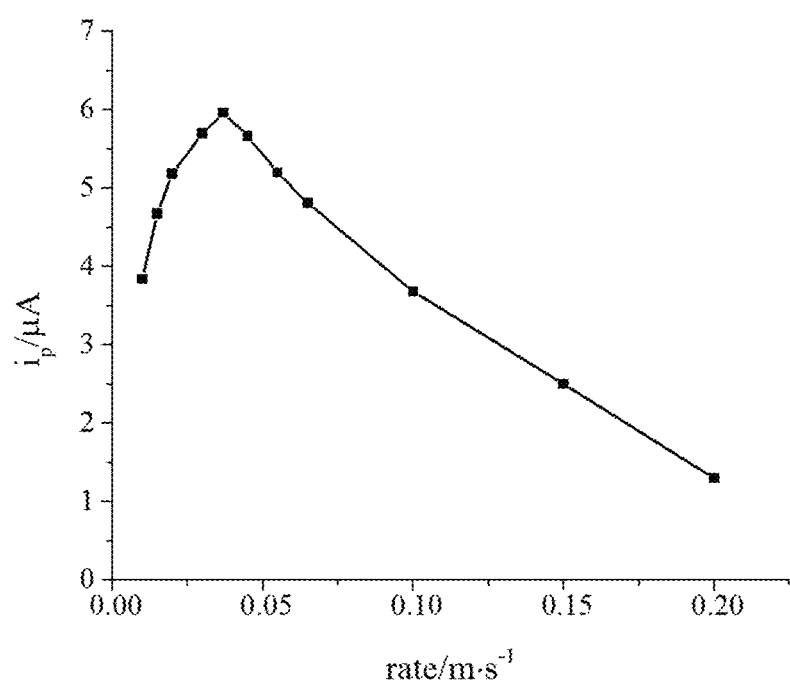
FIG. 30 is a stripping peak current line graph of $Pb^{2+}$ in different flow rates.

Experimental detection is carried out for micro-channel thickness and pipeline flow rate referring to the detection means and parameters in the above embodiment for detection of a single heavy metal ions Pb2+: firstly, the Pb$^{2+}$ sample with concentration of 60 μg/L is detected under different micro-channel thicknesses, so as to obtain stripping peak currents as shown in FIG. 29, with the detected micro-channel thickness in the range of 0.1 mm to 2.5 mm; the results show that the thickness range of 0.8 mm to 1.2 mm is the range with the highest stripping peak current, where the highest stripping peak value corresponds to the micro-channel thickness of 0.9 mm; then a micro-channel with thickness of 0.9 mm is selected, and different flow rates in the enrichment process are set by adjusting the peristaltic pump, so as to obtain the stripping peak currents as shown in FIG. 30, with the detected flow rate in the range of 0.01 m/s to 0.3 m/s; the results show that the flow rate range of 0.02 m/s to 0.05 m/s is the range with the highest stripping peak current, where the highest stripping peak value corresponds to the flow rate of 0.037 m/s. According to the above experimental results, the basic technical scheme of the above detection selects the optimal micro-channel thickness of 0.9 mm and the optimal pipeline flow rate of 0.037 m/s, with the pipeline inner diameter of 0.83 mm, slightly less than the micro-channel thickness; the converted flow rate is 1.2 mL/min which is maintained by setting the speed of the peristaltic pump.

The card electrode in the device of the present invention can be further improved:

the working area of the electrode is generally in conventional square or circular design, such as the three-electrode design shown in FIG. 31. In the pre-electrolysis process of ASV detection, the planar electrode with a surface having solution laminar flow has the following electrolysis current:

$$I_t = 0.68 n F D_i^{\frac{2}{3}} c_0 b L^{\frac{1}{2}} u^{\frac{1}{2}} v^{-\frac{1}{6}}$$

in the above formula, L is the size of an electrode parallel to the direction of the laminar flow; b is the size of an electrode perpendicular to the direction of the laminar flow; u is the flow rate of the solution; v is the kinematic viscosity of the solution. According to the formula, the electrolysis current can be increased by increasing the flow rate and the electrode area, which is advantageous to improve the pre-electrolysis efficiency, but a too large electrode area may cause the current density to be smaller and the background noise to be larger, which is extremely detrimental to the quantitative analysis; thus, it is considered, with the premise of not enlarging the electrode area, to design the shape of the electrode so as to make its effective working zone positioned in an area with higher solution flow rate. The card electrode 1 shown in FIG. 3 is taken as an example, which is used with the saddle-shaped micro-channel 22: after the card electrode 1 is inserted into a thin-layer flow cell 2, the micro-channel area 15 on the card electrode 1 enters the micro-channel 22, and then the portions of three electrodes located within the micro-channel area 15 are the effective working zone of the electrode.

As shown in FIG. 25b, two ideal working zones Z1 and Z2 of the electrode exist in a simulation flow field of the saddle-shaped micro-channel 22, and form an S shape in the micro-channel 22, wherein the zone close to the orifice of the liquid inlet pipeline 221 and positioned on the lower half part of the S shape has the highest flow speed, and is the ideal working zone Z1; the zone close to the orifice of the liquid outlet pipeline 222 and positioned on the upper half part of the S shape has low but nearly stable flow speed, and is the ideal working zone Z2. Effective working zones of the three electrodes on the substrate of the card electrode are improved and designed into shapes distributed along the abovementioned S-shaped ideal working zones, the improved shapes of the three electrodes are shown in FIG. 32a, FIG. 32b and FIG. 32c, and respectively correspond to the situation in which the three electrodes are distributed on the lower half part of the S shape, the upper part of the S shape and the whole S-shaped zone. The saddle-shaped dashed zone in the figures is the micro-channel area 15, the three contact pins 13 of the card electrode are vertically distributed below the micro-channel area 15 in parallel, in the above micro-channel area 15, the electrode connected with the leftmost contact pin is the counter electrode, the electrode connected with the middle contact pin is the working electrode, and the electrode connected with the rightmost contact pin is the reference electrode. After the electrodes adopt the abovementioned improved shapes, in particular when the effective working zone of the electrode shown in the FIG. 32c is positioned in the whole S-shaped ideal working zone of the flow field, better action time and ideal stability can be obtained under the condition that the overall area of the electrode is not increased, which is beneficial for improving the sensitivity and reproducibility of the detection.

Figures 33A, 33B, 33C:
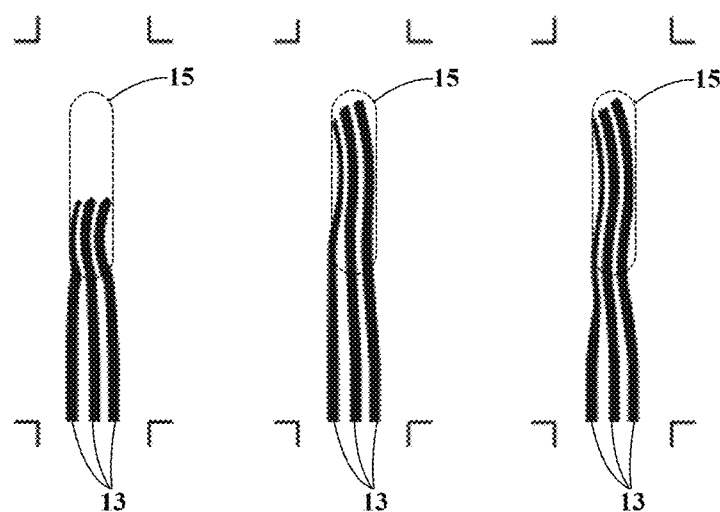
FIG. 33A is a design diagram of an S-shaped tri-electrode further improved by the present invention, wherein the electrode is the lower part of an S shape.
FIG. 33B is a design diagram of an S-shaped tri-electrode further improved by the present invention, wherein the electrode is the upper part of the S shape.
FIG. 33C is a design diagram of an S-shaped tri-electrode further improved by the present invention, wherein the electrode is the entire S shape.

The three electrodes on the card electrode of the present invention have two working states during detection: a voltage is applied between the working electrode and the reference electrode for carrying out electrolysis when the solution is in a flowing state during the enrichment process; a current is detected between the working electrode and the counter electrode when the solution is in a static state during the stripping process. The design of the electrode of the present invention aims at improving the electrolysis enrichment efficiency of the electrode under the solution flowing state, therefore, the areas of the working electrode and the reference electrode need to be increased, while when the counter electrode is in operation, the solution is in the static state, and is not sensitive to the area and the shape, therefore, further improvement can be made on the basis of the abovementioned improved shape of the electrode, the working electrode in the middle and the reference electrode on the right side are thickened to have the width equal to that of the contact pins, the counter electrode on the left side remains the original width and slightly deviates from the original position to make room for the other two electrodes; in addition, the connecting portions flexing outwards between the electrodes on the left and right sides and the contact pins are rounded. As shown in FIGS. 33a, 33b and 33c, the electrodes in the FIGS. 32a, 32b and 32c are designed to have the shapes of the above further improvement.

The card electrode of the present invention shown in FIG. 3 is taken as a sample, the card electrode 1 needs to be connected with the electrochemical analysis work station during detection, the interface end 14 of the card electrode 1 can be designed to be a plug matched with the standard USB jack. As the standard USB jack has four contact pins, while the interface end 14 of the card electrode 1 only has three contact pins 13 connected with the electrodes, therefore, only the position and the size of the contact pins 13 need to be arranged to enable the three contact pins 13 to respectively contact three of the four contact pins of the USB jack after the card electrode 1 is inserted into the standard USB jack. After the interface end 14 is inserted into the USB interface, three corresponding connecting lines in the USB jack are respectively connected with electrode holders of the electrochemical analysis work station, and thus the three electrodes of the card electrode 1 are connected on the electrochemical analysis work station. As the USB interface is the most common communication device, the design of the interface end can enable the compatibility of the electrode card with a connected device to be stronger, and thus the field rapid detection is facilitated.

It should be understood that, the aforementioned embodiments are merely used for illustrating the technical thoughts and features of the present invention, for enabling those skilled in the art to understand the contents of the present invention and implement the contents accordingly, the aforementioned embodiments are not exhaustion of specific embodiments, and the scope of protection of the present invention cannot be limited hereto. Any modifications or equivalent substitutions made according to the technical solutions of the present invention, without departing from the spirit and scope of the technical solutions of the present invention, shall fall within the scope of claims of the present invention.

What is claimed is:

1. A portable rapid detection device for heavy metal ions, comprising: a card electrode (1) and a thin-layer flow cell (2), wherein:
    the card electrode (1) comprises a substrate (11) and a three-electrode system; the three-electrode system comprises a working electrode (121), a counter electrode (122) and a reference electrode (123) which are planar all-solid-state electrodes distributed on the substrate (11); one end of the substrate (11) is an interface end (14), contact pins (13) are distributed on the interface end (14), and the three contact pins are respectively connected with the three electrodes of the three-electrode system;
    the thin-layer flow cell (2) is of an integrally formed structure and comprises a cell wall (21), a micro-channel (22) and an electrode socket (23); the micro-channel (22) is a thin-layer-shaped cavity enclosed by the cell wall (21), and the micro-channel (22) is connected with a liquid inlet pipeline (221) and a liquid outlet pipeline (222) which lead outwards; the electrode socket (23) is an opening of the micro-channel (22) on the cell wall (21), and the card electrode (1) can be inserted in and pulled out from the electrode socket (23); and
    the card electrode (1) is inserted in the thin-layer flow cell (2) from the electrode socket (23), the three-electrode system stretches into the micro-channel (22), and the interface end (14) extends out of the cell wall (21);
    wherein the material of the thin-layer flow cell (2) is photosensitive resin and the thin-layer flow cell (2) is made by using a stereo lithography.

2. The portable rapid detection device for heavy metal ions according to claim 1, characterized in that the printing of the card electrode (1) is by using a silk-screen printing method.

3. The portable rapid detection device for heavy metal ions according to claim 1, characterized in that the contact pins (13) are arranged at the interface end (14) in parallel, and the sizes of the contact pins (13) are consistent with that of a standard USB interface.

4. The portable rapid detection device for heavy metal ions according to claim 1, characterized in that the working electrode (121) is a silver-carbon electrode, the counter electrode (122) is a silver electrode, and the reference electrode (123) is a silver-silver chloride electrode.

5. The portable rapid detection device for heavy metal ions according to claim 1, characterized in that the shape of the cavity of the micro-channel (22) is a rectangular shape, a saddle shape, an oval shape or a circular shape.

6. The portable rapid detection device for heavy metal ions according to claim 5, characterized in that the shape of the cavity of the micro-channel (22) is a saddle, and the liquid inlet pipeline (221) and the liquid outlet pipeline (222) are respectively connected with the micro-channel (22) at two top ends of the saddle-shaped cavity along the tangential direction.

7. The portable rapid detection device for heavy metal ions according to claim 1, characterized in that the liquid inlet pipeline (221) and the liquid outlet pipeline (222) are provided with pipeline orifices protruding from the outer wall of the cell wall (21).

8. The portable rapid detection device for heavy metal ions according to claim 1, characterized in that the thickness of the micro-channel (22) is 0.8 mm to 1.2 mm, and the inside diameters of the liquid inlet pipeline (221) and the liquid outlet pipeline (222) are smaller than or equal to the thickness of the micro-channel (22).

9. The portable rapid detection device for heavy metal ions according to claim 8, characterized in that the thickness of the micro-channel (22) is 0.9 mm, and the inside diameters of the liquid inlet pipeline (221) and the liquid outlet pipeline (222) are 0.83 mm.

10. The portable rapid detection device for heavy metal ions according to claim 9, characterized in that the three electrodes of the three-electrode system are distributed on the substrate (11) along the flow field shape of a solution to be detected in the micro-channel (22).

11. The portable rapid detection device for heavy metal ions according to claim 10, characterized in that the widths of the working electrode (121) and the reference electrode (123) are greater than that of the counter electrode (122).

12. The portable rapid detection device for heavy metal ions according to claim 6, characterized in that the flow field of the solution to be detected in the saddle-shaped micro-channel (22) is S-shaped at a flow rate between 0.02 and 0.05 m/s, and the three electrodes of the three-electrode system are distributed on the substrate (11) along the S-shaped flow field.

13. A method for utilizing the portable rapid detection device of claim 1, comprising the following specific steps:
    (1) assembly of a detection system: connecting the liquid inlet pipeline and the liquid outlet pipeline of the thin-layer flow cell to a liquid inlet hose and a liquid outlet hose, respectively, wherein the liquid inlet hose extends into the solution to be detected and is provided with a peristaltic pump, and connecting the interface end of the card electrode with a corresponding interface of an electrochemical analysis workstation;
    (2) an enrichment process: adjusting the electrochemical analysis workstation, and applying an enrichment voltage between the working electrode and the reference electrode; starting the peristaltic pump, driving the solution to be detected to flow into the thin-layer flow cell from the liquid inlet pipeline for pre-electrolysis, and discharging waste liquid from the liquid outlet pipeline; after the pre-electrolysis, shutting down the peristaltic pump, and standing the solution to be detected;
    (3) a stripping process: adjusting the electrochemical analysis workstation to positively scan the voltage between the working electrode and the reference electrode from a negative direction, so that heavy metals to be detected and enriched on the working electrode are stripped again; and
    (4) detection data collection: recording the current in the working electrode and an auxiliary electrode circuit and the potential of the working electrode in the stripping process to obtain a stripping voltammetry curve.

14. The method according to claim 13, characterized in that a $Bi^{3+}$ solution and an acid base solution are added in the solution to be detected and containing heavy metal ions before detection.

15. The method according to claim 14, characterized in that the concentration of $Bi^{3+}$ in the solution to be detected is 500 μg/L.

16. The application method according to claim 14, characterized in that the acid base solution is a 0.1 mol/L NaAc—HAc solution, and the pH of the solution to be detected is adjusted to be 4.6.

17. The method according to claim 13, characterized in that in the enrichment process, the flow rate of the solution to be detected in the liquid inlet pipeline is set as 0.02 m/s to 0.05 m/s.

18. The method according to claim 13, characterized in that the enrichment voltage is −1.2V, the enrichment time for finishing the enrichment process is 180 s, and the enrichment time contains a standing time of 60 s.

19. The method according to claim 13, characterized in that in the stripping process, the voltage is scanned by square waves, and the potential increment is 0.005V.

\* \* \* \* \*